US012682205B2

(12) United States Patent  
Torkamani et al.

(10) Patent No.: US 12,682,205 B2  
(45) Date of Patent: Jul. 14, 2026

(54) DIFFERENTIAL EQUATIONS NETWORK

(71) Applicant: Cambia Health Solutions, Inc.,  
Portland, OR (US)

(72) Inventors: Mohamadali Torkamani, Portland, OR  
(US); Phillip Wallis, Portland, OR (US)

(73) Assignee: CAMBIA HEALTH SOLUTIONS,  
INC., Portland, OR (US)

( * ) Notice: Subject to any disclaimer, the term of this  
patent is extended or adjusted under 35  
U.S.C. 154(b) by 1361 days.

(21) Appl. No.: 16/160,933

(22) Filed: Oct. 15, 2018

(65) Prior Publication Data

US 2019/0114531 A1 Apr. 18, 2019

Related U.S. Application Data

(60) Provisional application No. 62/631,379, filed on Feb.  
15, 2018, provisional application No. 62/572,110,  
filed on Oct. 13, 2017.

(51) Int. Cl.  
*G06N 3/04* (2023.01)  
*G06N 3/048* (2023.01)  
*G06N 3/084* (2023.01)  
*G16H 20/40* (2018.01)  
*G16H 50/30* (2018.01)

(52) U.S. Cl.  
CPC ............... *G06N 3/04* (2013.01); *G06N 3/048*  
(2023.01); *G06N 3/084* (2013.01); *G16H*  
*20/40* (2018.01); *G16H 50/30* (2018.01)

(58) Field of Classification Search  
CPC .......... G06N 3/04; G06N 3/0481; G06N 3/08;  
G06N 3/084; G06N 3/048; G06N 3/0464;  
G06N 3/0495; G06N 3/09; G06N 3/094;  
G16H 20/40; G16H 50/30; Y02A 90/10  
See application file for complete search history.

(56) References Cited

U.S. PATENT DOCUMENTS

| | | | |
|---|---|---|---|
| 5,280,564 A | 1/1994 | Shiomi et al. | |
| 5,299,285 A | 3/1994 | Tawel | |
| 2013/0041859 A1 | 2/2013 | Esterlilne | |
| 2017/0032241 A1* | 2/2017 | Corrado ................ | G16H 50/30 |
| 2017/0249547 A1* | 8/2017 | Shrikumar ............. | G06N 3/045 |
| 2018/0053086 A1* | 2/2018 | Liu ........................ | G06N 3/048 |
| 2018/0144245 A1* | 5/2018 | Simard .................. | G06N 3/084 |
| 2020/0279129 A1* | 9/2020 | Batchelor .............. | G06V 20/52 |

OTHER PUBLICATIONS

Hagge, T. et al. "Solving differential equations with unknown constitutive relations as recurrent neural networks" (Year: 2017).*  
Chiaramonte, M. M. et al. "Solving differential equations using neural networks" (Year: 2013).*

(Continued)

*Primary Examiner* — Alexey Shmatov  
*Assistant Examiner* — Devika S Maharaj  
(74) *Attorney, Agent, or Firm* — McCoy Russell LLP

(57) ABSTRACT

Methods and systems are provided for a differential equations network. In one example, the differential equations network comprises one or more neuron within a single neural layer, where each of the neurons is configured to learn an activation function different or similar to an activation function learned by a different neuron within the same layer.

17 Claims, 16 Drawing Sheets

(56)          References Cited

OTHER PUBLICATIONS

Lagaris, I. E. et al., "Artificial Neural Networks for Solving Ordinary and Partial Differential Equations" (Year: 1997).*

Harmon, M. et al. "Activation Ensembles for Deep Neural Networks" (Year: 2017).*

Meade, A.J. et al., "The Numerical Solution of Linear Ordinary Differential Equations by Feedforward Neural Networks" (Year: 1994).*

Wikipedia, "Multilayer Perceptron", https://en.wikipedia.org/wiki/Multilayer_perceptron.*

Agostinelli, F. et al., "Learning Activation Functions to Improve Deep Neural Networks", https://arxiv.org/abs/1412.6830 (Year: 2015).*

Turner, A. et al., "Neuro Evolution: Evolving Heterogeneous Artificial Neural Networks", https://link.springer.com/article/10.1007/s12065-014-0115-5 (Year: 2014).*

Torkamani, M. et al., "Differential Equation Networks," ICLR 2019 Conference Blind Submission, Open Review Website, Available Online at https://openreview.net/forum?id=r1xwS3RqKQ, Sep. 27, 2018, 11 pages.

* cited by examiner

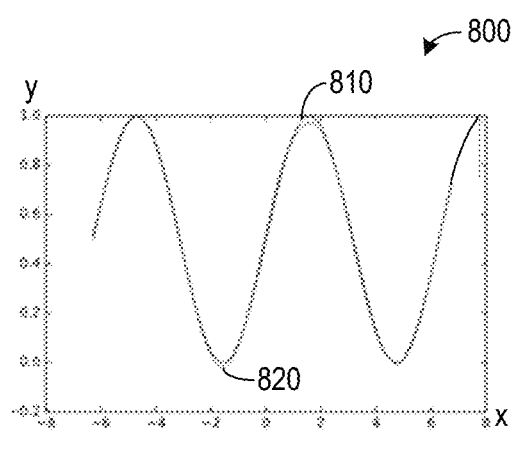
FIG. 8A
FIG. 8B
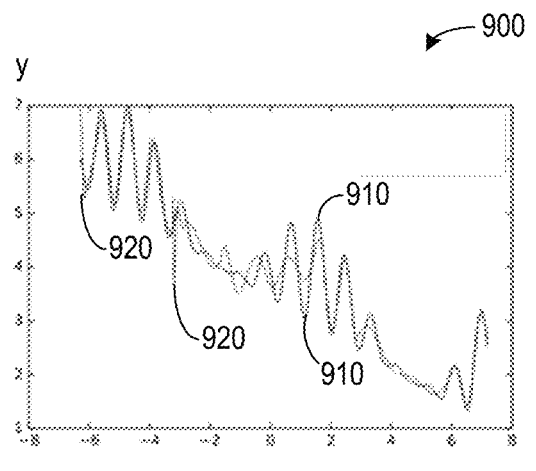
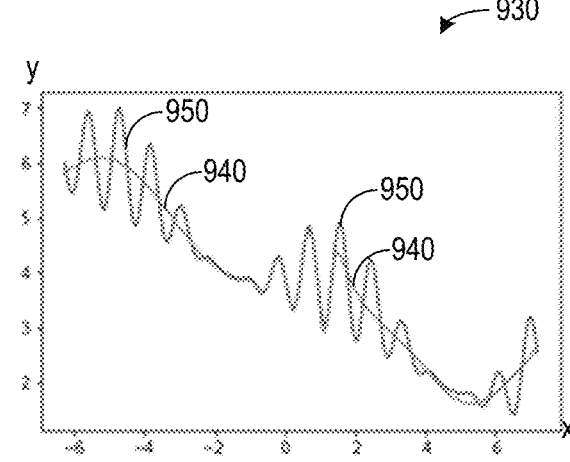
FIG. 9A
FIG. 9B
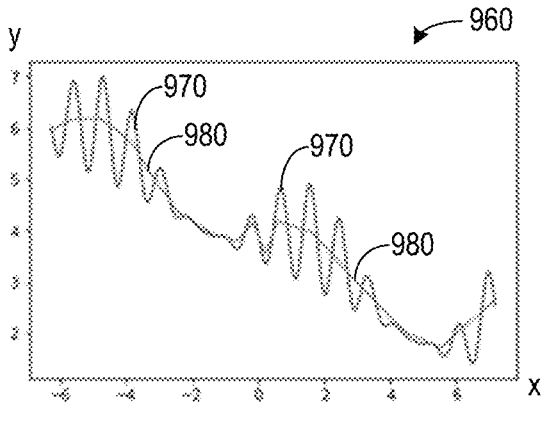
FIG. 9C

DIFFERENTIAL EQUATIONS NETWORK

CROSS REFERENCE TO RELATED APPLICATIONS

The present application claims priority to U.S. Provisional Application No. 62/572,110, entitled "DIFFERENTIAL EQUATIONS NETWORK", and filed on Oct. 13, 2017. This present application also claims priority to U.S. Provisional Application No. 62/631,379, entitled "DIFFEREN-TIAL EQUATIONS NETWORK", and filed on Feb. 15, 2018. The entire contents of the above-listed applications are hereby incorporated by reference for all purposes.

FIELD

The present description relates generally to a differential equations network having independently operating neurons.

BACKGROUND AND SUMMARY

Deep neural networks (DNNs) may realize solutions to more complex tasks than shallow neural networks due to advancements in storage, processing, and parallel computing. Many applications that employ DNNs, such as image classification, speech recognition, and machine translation demand immense computational resources and time to train, even with GPUs and large scale parallel processing. The computational resources that may be used for machine learning utilizing DNNs may include cloud computing and GPUs.

For example, the size of a neural network may be delineated by the number of hidden neurons in the network, and by their interrelationship, which together determine the network complexity. The ideal size of a network depends on the intricacy of the concept it is needed to learn. A network that is too small may not be capable of fully and circumstantially learning a problem or even parts of it.

Thus, as networks evolve and become capable of solving more intricate problems, computational processing, storage, and the costs thereof may become issues. In this way, more complex problems may demand larger neural networks, thereby increasing an operating cost to maintain the larger neural network.

Previous examples of neural networks may include networks comprising multiple hidden layers of neurons, where each layer may comprise 100 or more neurons. Each hidden layer of neurons may be assigned a single activation function such that each neuron of the hidden layer learns the single activation function. For example, if a neural network has five hidden layers, then the neural network may learn up to five different activation functions, each of the activation functions being assigned to a single hidden layer of the five hidden layers. The downfall of neural networks of this type may be size, efficiency, and speed. A neural network of this size may demand a relatively large amount of storage (e.g., memory), which may increase a cost to a consumer. Additionally, network efficiency and speed may decrease as network size increases. In this way, solving complex problems may be slow and inefficient.

The inventors recognize the above described issues and have come up with a solution to at least partially address them. In one example, a method for performing differential equations network (DEN) computations for a DEN having a plurality of DEN layers, the method comprising obtaining, from n input neurons along n dimensions of the DEN, n activation functions for n neurons of a hidden neural network layer of the DEN and selecting an activation function of the n activation functions to teach to a neuron of the n neurons, where each neuron of the n neurons learns one of the n activation functions. In this way, each neuron within the single layer may learn an activation function different than other neurons within the same layer.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 4A, 4B, 4C, 4D, 4E, 4F, 4G, 4H, 4I, and 4J show various activation functions when values of the activation function are restricted to values in a set.

FIGS. 8A and 8B show plots depicting a differential equations network having two neurons and a neural network having 20 neurons, respectively.

FIGS. 9A, 9B, and 9C show plots depicting a differential equations network having 15 neurons and neural networks having 100 neurons, respectively.

DETAILED DESCRIPTION

The following description relates to a differential equations network (FIG. 2) comprising at least one hidden neural layer comprising two or more neurons. The differential equations network may be arranged on a computing system (FIG. 1), the computing system comprising instructions stored on memory thereof configured to allow the neurons of the neural layer to learn one or more activation functions independently of one another.

Figure 3B:
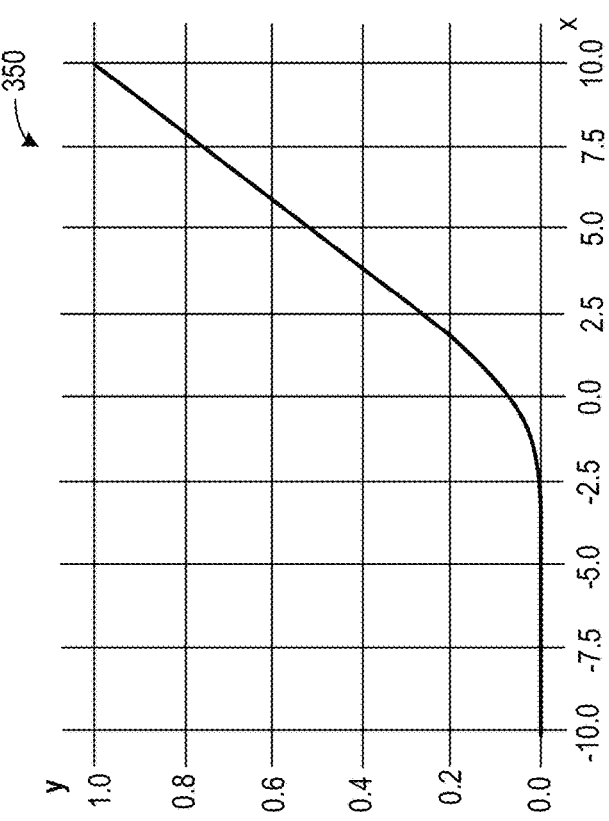
FIGS. 3A and 3B show sigmoid and ReLU activation functions, respectively.
Figure 3A:
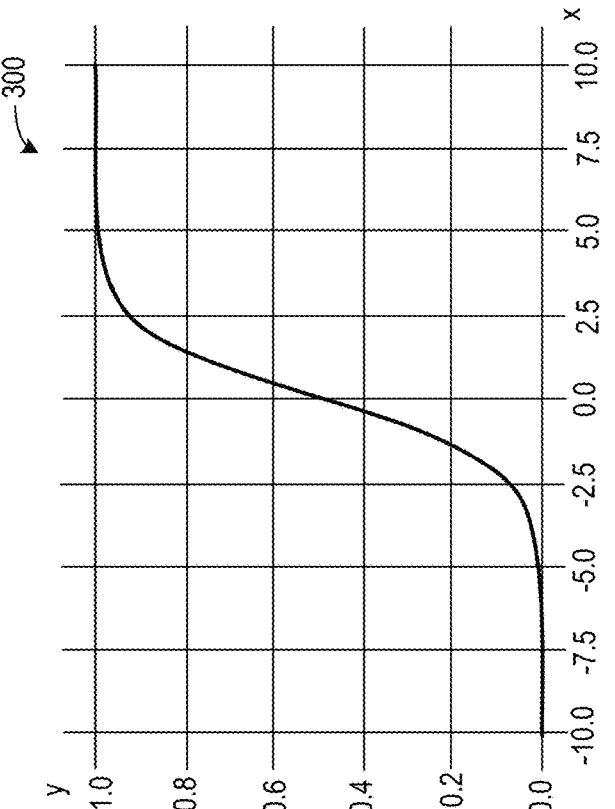

In the description below, it will become readily apparent as to the benefits achieved by the differential equations network compared to a deep neural network (DNN). Common activation functions are shown in FIGS. 3A and 3B. These activation functions may be associated with DNNs, wherein every neuron in a single hidden layer learns the same activation function. This is in contrast to the activation functions of FIGS. 4A, 4B, 4C, 4D, 4E, 4F, 4G, 4H, 4I, and 4J, which show a plurality of different activation functions configured to be learned by one or more neurons of a single layer in a differential equations network. FIGS. 5A, 5B, 5C, 5D, and 5E also show other examples of activation functions which may be learned by the neurons of a single layer of a differential equations network. That is to say, neurons of the single layer of the differential equations network may learn different activation functions while being arranged in the same layer. For example, a first neuron of a first hidden layer may learn the activation function of FIG. 4D and a second neuron of the first hidden layer may learn the activation function of FIG. 4H.

Figure 6A:
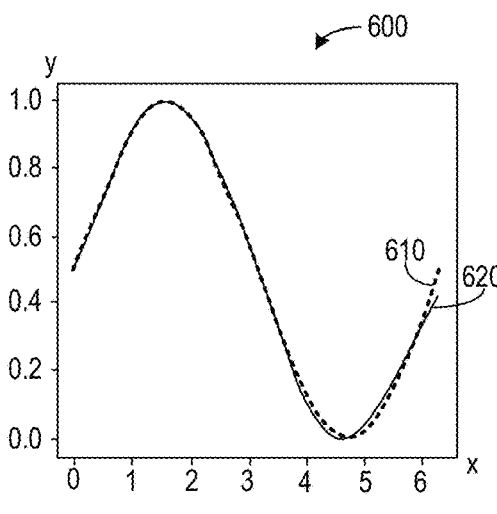
FIGS. 6A and 6B show plots depicting a fixed activation feed-forward neural network and a differential equations network, respectively.
Figure 6B:
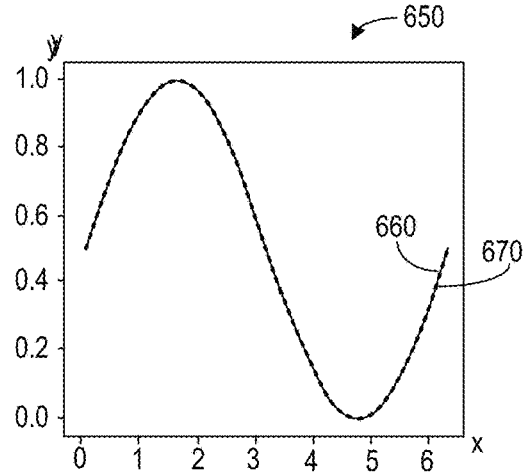
Figure 7A:
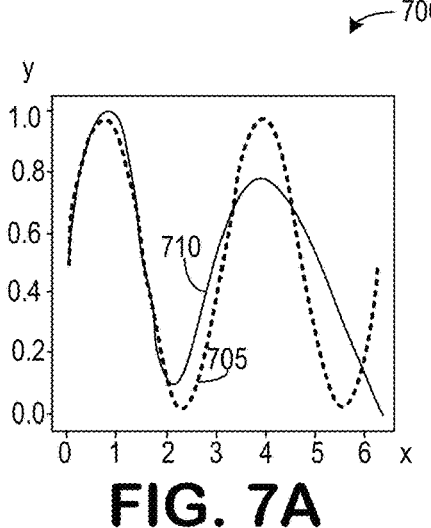
FIGS. 7A, 7B, and 7C show plots depicting a fixed activation neural network having a single hidden layer comprising 100 neurons, a fixed activation neural network having two hidden layers each comprising 100 neurons, and a differential equations network having a single hidden layer comprising three neurons, respectively.
Figure 7B:
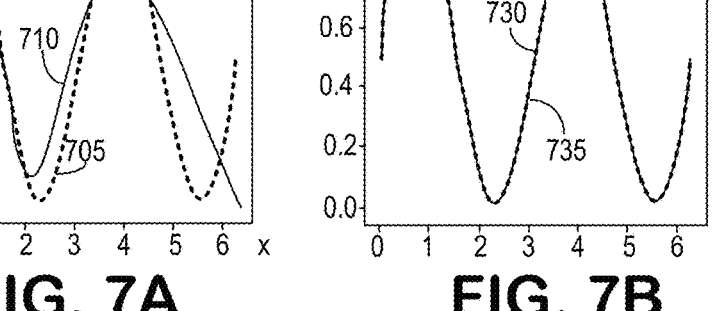
Figure 7C:
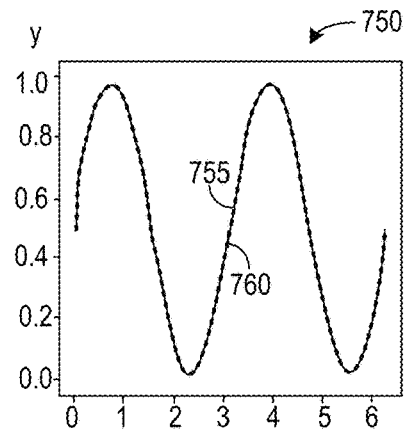

FIGS. 6A and 6B compare an actual function output with predicted outputs of a DNN and a differential equations network, respectively. In one example, the DNN is a fixed activation feed-forward neural network (FFNN). FIGS. 7A, 7B, and 7C depict a FFNN having 100 neurons in a single layer, a FFNN having 200 neurons split among two layers, and a differential equations network having three neurons in a single layer, respectively. These comparisons are to illustrate the problem solving aptitude of the differential equations network relative to the DNN.

Figure 13:
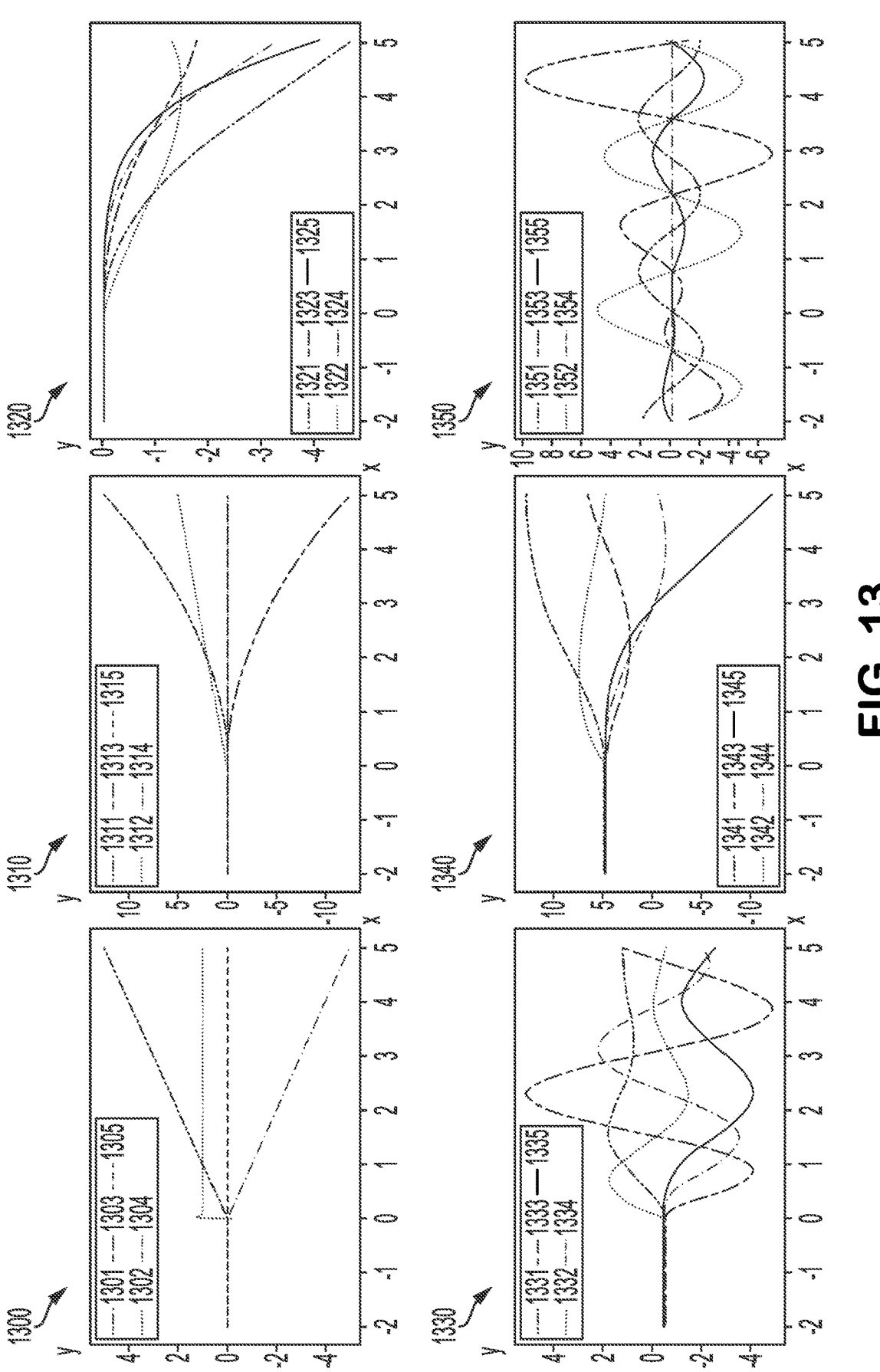
FIG. 13 depicts a plurality of differential equations network activation functions with a plurality of derivatives.
Figure 14:
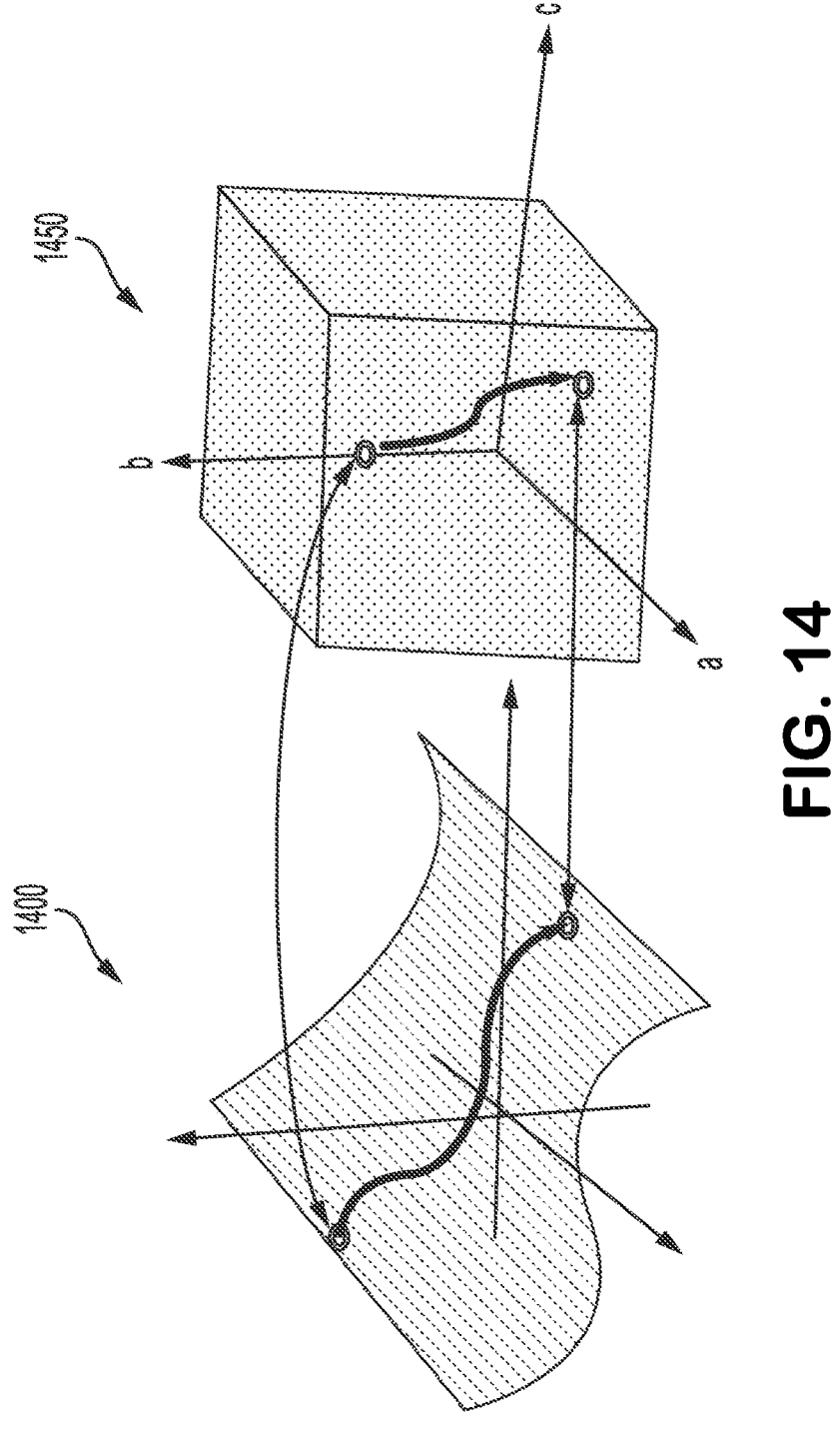
FIG. 14 depicts a function transforming to another function utilizing the algorithm disclosed herein.
Figure 15:
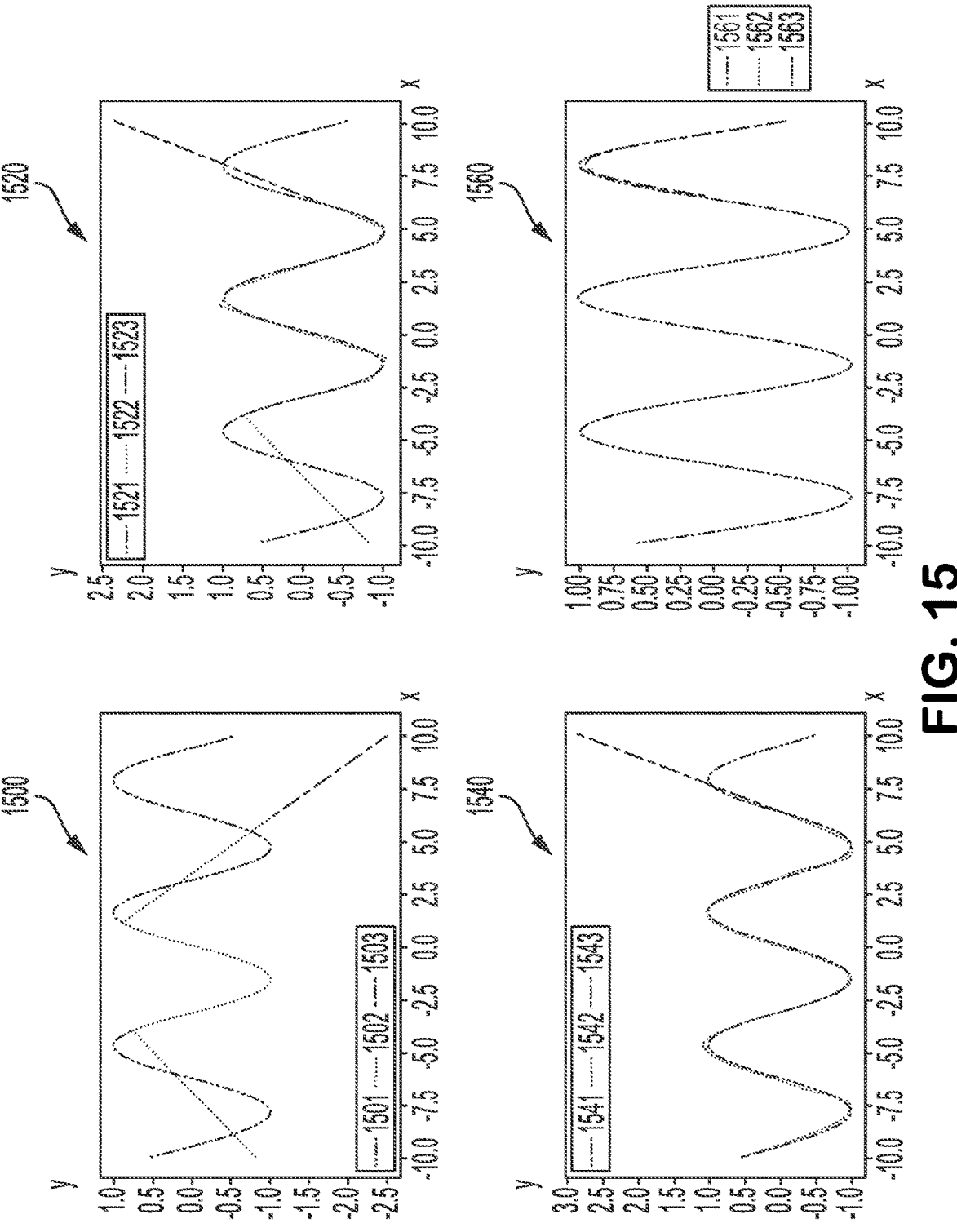
FIG. 15 illustrates a plurality of plots depicting fixed activation function networks and a differential equations network approximating a sine function.
Figure 16:
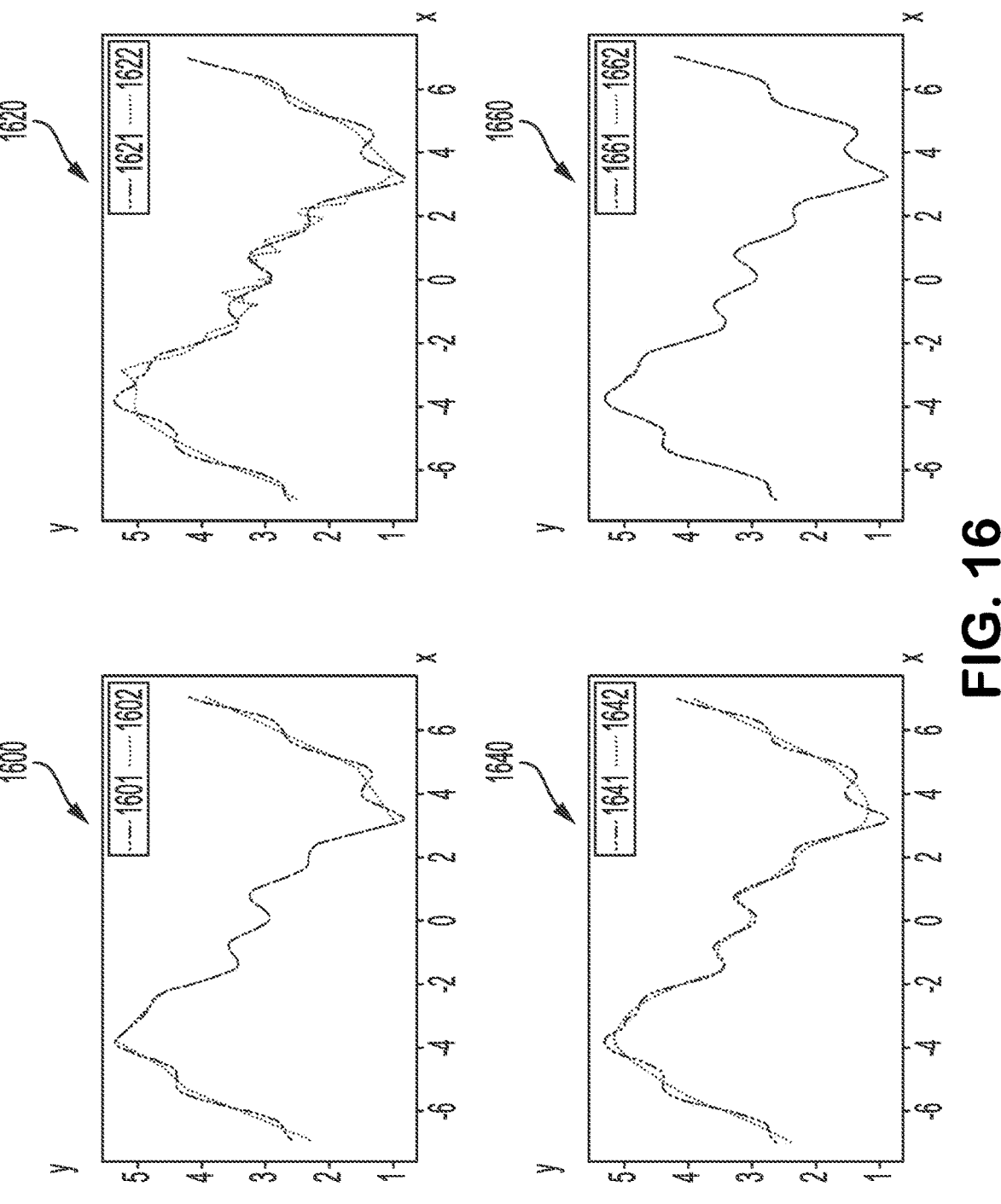
FIG. 16 illustrates a plurality of plots depicting fixed activation function networks and a differential equations network approximating a sine function.
Figure 17:
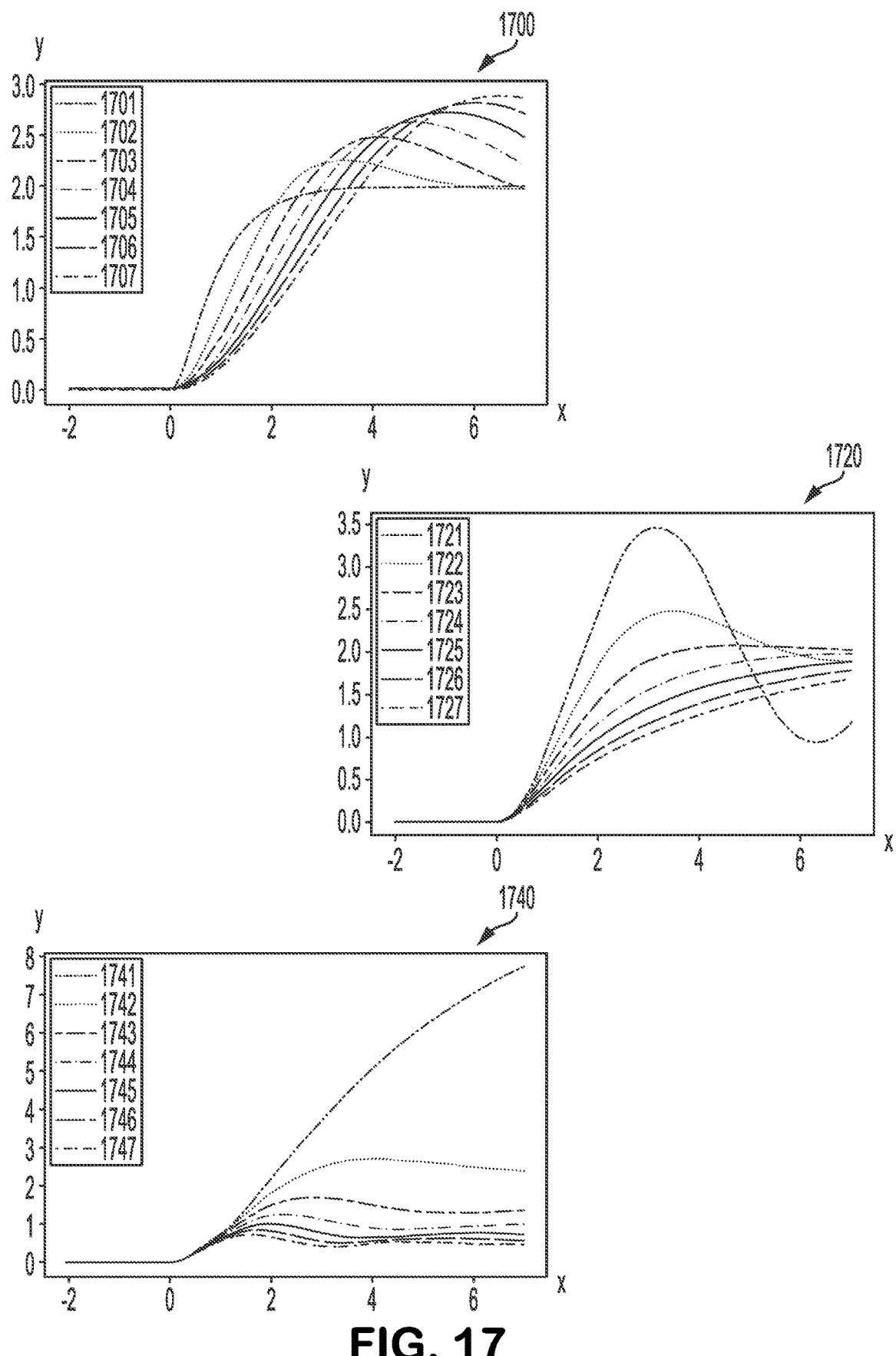
FIG. 17 illustrates a plurality of activation functions learnable by neurons of a differential equations network.

FIGS. 8A, 8B, 9A, 9B, and 9C further demonstrate the problem solving capabilities of the differential equations network. Therein, the figures compare predicted outputs of the differential equations network and predicted outputs of a neural network, wherein the differential equations network is smaller than the neural network. In one example, smaller may refer to a number of neurons, wherein the smaller differential equations network comprises fewer neurons than the larger neural network. FIG. 13 depicts a plurality of differential equations network activation functions with a plurality of derivatives. FIG. 14 depicts a transformation of a differential equation network. FIG. 15 illustrates a plurality of plots depicting fixed activation function networks and a differential equations network approximating a sine function. FIG. 16 illustrates a plurality of plots depicting fixed activation function networks and a differential equations network approximating a sine function. FIG. 17 illustrates a plurality of activation functions learnable by neurons of a differential equations network.

Figure 10:
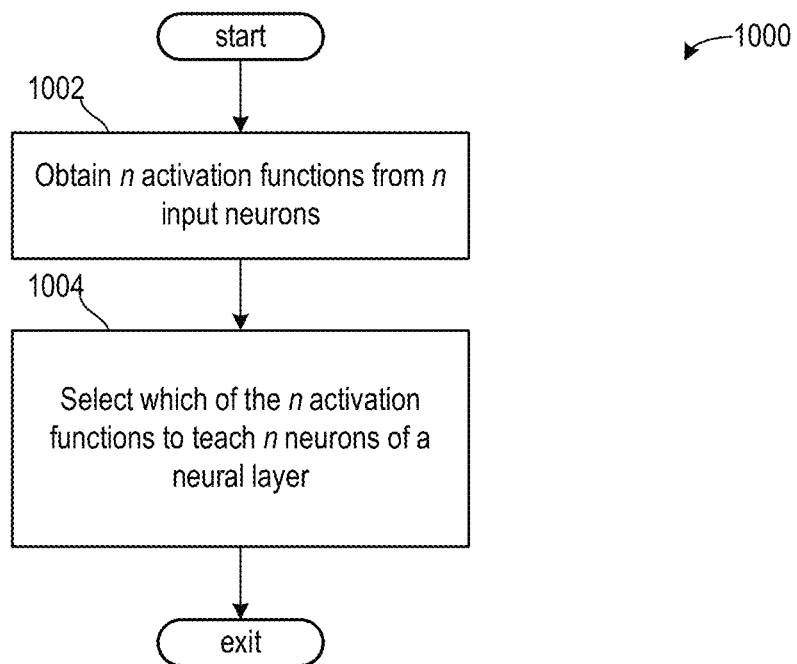
FIG. 10 depicts a high-level flow chart for a hidden neural network layer receiving activation functions from an input layer.
Figure 11:
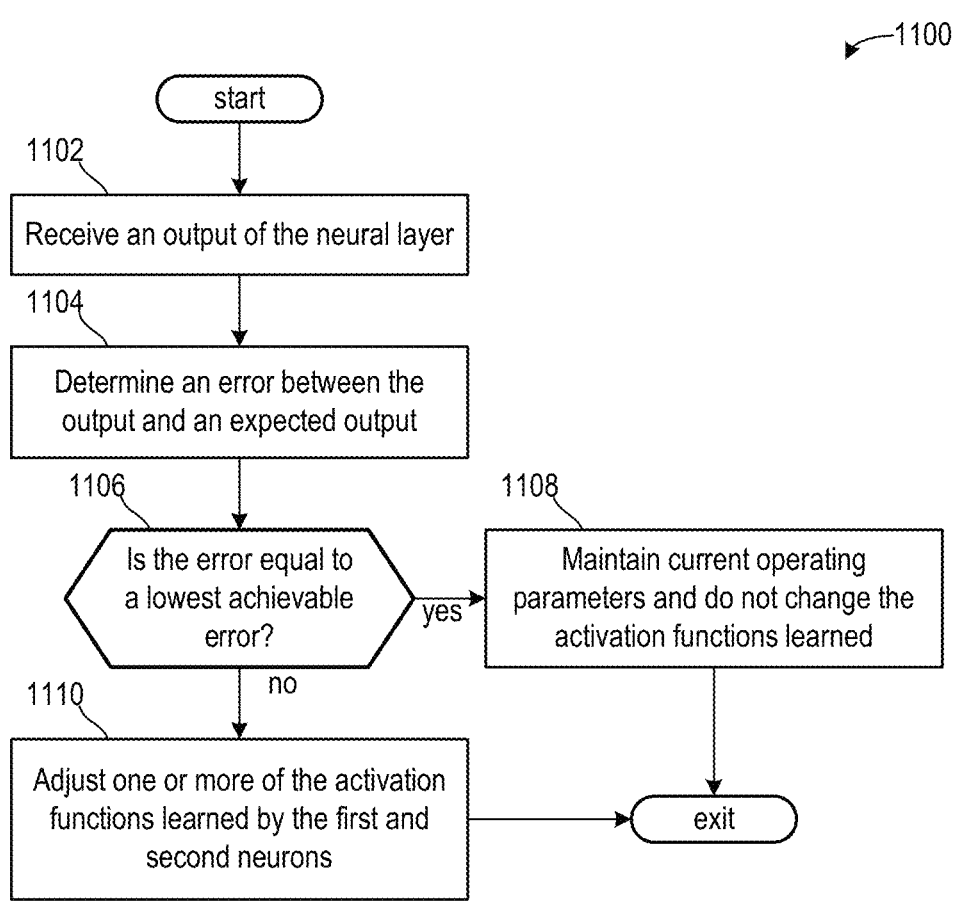
FIG. 11 depicts a flow chart for determining which of the activation functions the two or more neurons are to learn based on an error between an output of the neurons and an expected output.
Figure 12:
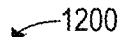
FIG. 12 depicts a flow chart predicting a healthcare plan via the differential equations network.
Figure 12:
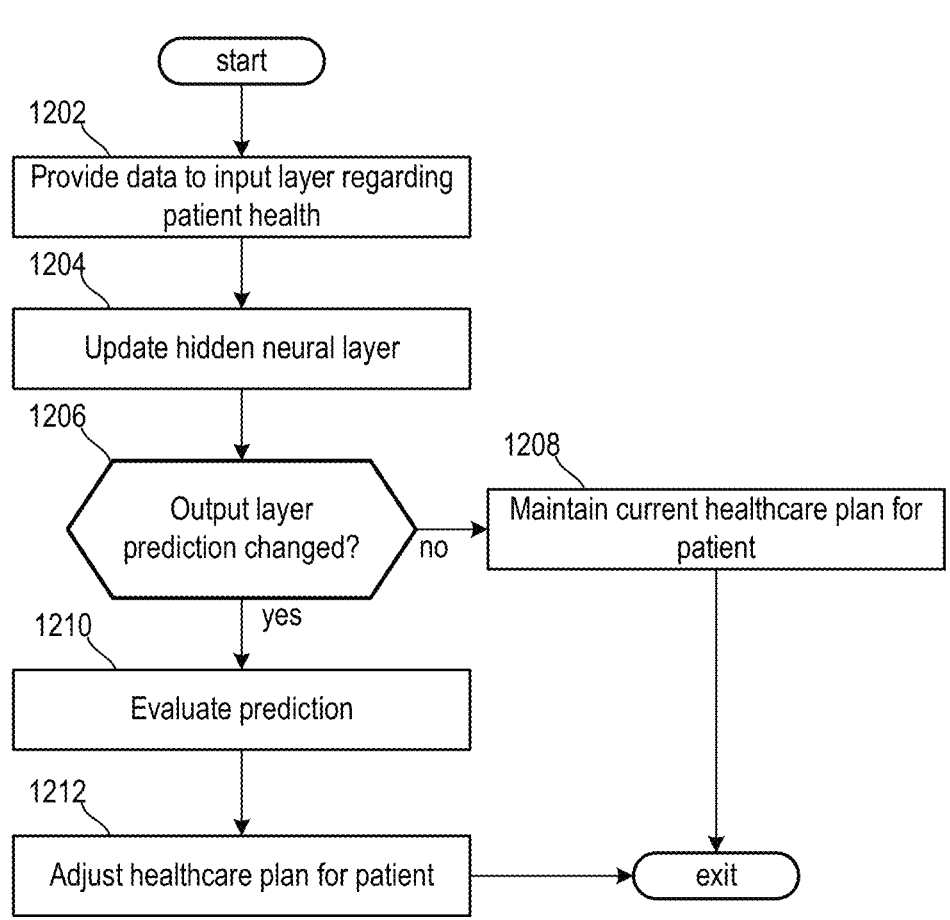

FIGS. 10 and 11 depict methods for providing activation functions to a hidden neural network layer comprising at least two or more neurons and selecting which of the activation functions the neurons are to learn based on an error between an output of the neurons and an expected output. FIG. 12 depicts a method for predicting outcomes based on a plurality of inputs received by the differential equations network. The inputs may be associated with patient health data, wherein the data is received by the differential equations network. Activation functions associated with the inputs may be learned by the neurons of the single hidden neural layer, wherein each neuron of the hidden neural layer learns a different activation of the activation functions provided. The activation functions are adjusted to decrease an error of a predicted outcome. The predicted outcome may be sent to a display of an electronic device, such as a phone, tablet, computer, or the like. The differential equations network may provide faster computing speeds at a fraction of the size relative to previous examples of neural networks, such as feed-forward neural networks and deep neural networks.

Figure 1:
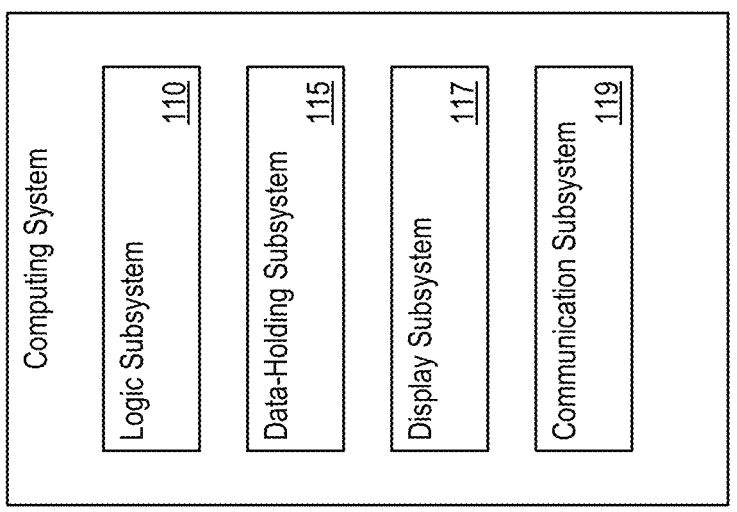
FIG. 1 shows a block schematic diagram of an example computing system for predicting multiple health care outcomes.

FIG. 1 schematically shows a non-limiting computing system 100 that may perform one or more of the methods and processes described herein. It is to be understood that virtually any computer architecture may be used for a computing device without departing from the scope of this disclosure. In different embodiments, computing system 100 may take the form of a mainframe computer, server computer, desktop computer, laptop computer, tablet computer, network computing device, mobile computing device, mobile communication device, and so on.

Computing system 100 includes a logic subsystem 110 and a data-holding subsystem 115. Computing system 100 may optionally include a display subsystem 117, communication subsystem 119, and/or other components not shown in FIG. 1. For example, computing system 100 may also optionally include user input devices such as keyboards, mice, cameras, microphones, and/or touch screens.

Logic subsystem 110 may include one or more physical devices configured to execute one or more instructions. For example, logic subsystem 110 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 110 may include one or more processors that are configured to execute software instructions. In one example, the processors are controllers. Additionally or alternatively, the logic subsystem 110 may include one or more hardware and/or firmware logic machines configured to execute hardware and/or firmware instructions. Processors of the logic subsystem 110 may be single core or multi-core, and the programs executed thereon may be configured for parallel or distributed processing. The logic subsystem 110 may optionally include individual components that are distributed throughout two or more devices, which may be remotely located and/or configured for coordinated processing. One or more aspects of the logic subsystem 110 may be virtualized and executed by remotely-accessible networked computing devices configured in a cloud computing configuration.

Data-holding subsystem 115 may include one or more physical, non-transitory devices configured to hold data and/or instructions executable by the logic subsystem 110 to implement the herein described methods and processes. When such methods and processes are implemented, the state of data-holding subsystem may be transformed (for example, to hold different data).

Data-holding subsystem 115 may include removable media and/or built-in devices. Data-holding subsystem 115 may include optical memory (for example, CD, DVD, HD-DVD, Blu-Ray Disc, etc.), and/or magnetic memory devices (for example, hard disk drive, floppy disk drive, tape drive, MRAM, etc.), and the like. Data-holding subsystem 115 may include devices with one or more of the following characteristics: volatile, nonvolatile, dynamic, static, read/write, read-only, random access, sequential access, location addressable, file addressable, and content addressable. In some embodiments, logic subsystem 110 and data-holding subsystem 115 may be integrated into one or more common devices, such as an application specific integrated circuit or a system on a chip.

It is to be appreciated that the data-holding subsystem 115 includes one or more physical, non-transitory devices. In contrast, in some embodiments, aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

When included, display subsystem 117 may be used to present a visual representation of data held by data-holding subsystem 115. As the herein described methods and processes change the data held by the data-holding subsystem 115, and thus transform the state of the data-holding subsystem 115, the state of display subsystem 117 may likewise be transformed to visually represent changes in the underlying data. Display subsystem 117 may include one or more display devices utilizing virtually any type of technology. Such display devices may be combined with logic subsystem 110 and/or data-holding subsystem 115 in a shared enclosure, or such display devices may be peripheral display devices.

When included, communication subsystem 119 may be configured to communicatively couple computing system 100 with one or more other computing devices. Communication subsystem 119 may include wired and/or wireless communication devices compatible with one or more different communication protocols. As non-limiting examples, communication subsystem 119 may be configured for communication via a wireless telephone network, a wireless local area network, a wired local area network, a wireless wide area network, a wired wide area network, etc. In some embodiments, communications subsystem 119 may allow computing system 100 to send and/or receive messages to and/or from other devices via a network such as the public Internet.

Figure 2:
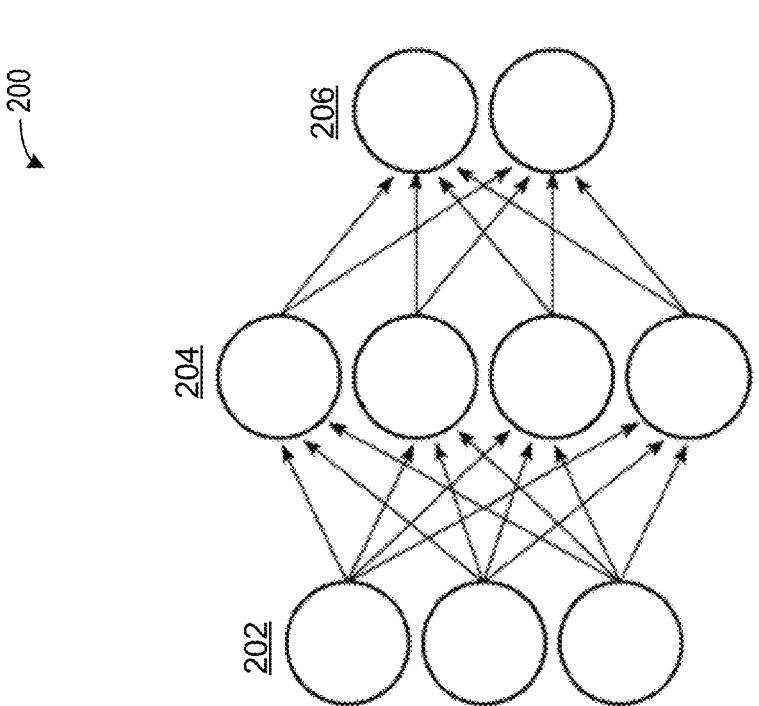
FIG. 2 shows a schematic diagram of an embodiment of a neural network.
Figure 2:

In the system of FIG. 2, a differential equations network 200 is shown. In one example, the differential equations network 200 is included in the computing system 100 of FIG. 1. The differential equations network 200 may comprise a plurality of interconnected neurons. For example, the differential equations network 200 may comprise a plurality of neurons in an input layer 202, a plurality of neurons in an output layer 206, and a plurality of neurons in a hidden layer 204. In one example, the neurons in the hidden layer 204 receive inputs and/or activation functions from the neurons in the input layer 202. These activation functions may alter an output of the neurons in the hidden layer 204 to the neurons in the output layer 206.

In some examples, the neurons and in any other layer of the differential equations network 200, may be configured such that each neuron of a specific layer (e.g., neurons in the hidden layer 204) may be configured to learn a desired activation function, wherein the activation function(s) may be received from the input layer 202. Specifically, each neuron of one or more layers is configured with the ability to learn its own activation function independently of other neurons within the same layer or in other layers. This may afford the differential equations network 200 a more compact (e.g., smaller) network than other networks (e.g., DNN) having uniform activation functions learned by all the neurons of a shared layer.

Thus, to solve the issues described above, the differential equations network 200 may comprise fewer neurons than a DNN having similar computing power and/or complexity. As such, the storage cost of the differential equations network 200 may be less than a DNN while achieving similar or greater problem solving capabilities.

For previous examples of the DNN, a layer of neuron may comprise a fixed activation function selected from one of the following equations:

$$\sigma(t) = \frac{1}{1+e^{-t}} ; \qquad \text{(equation 1)}$$

$$\mathrm{ReLu}\,(t) = \max(0, t); \qquad \text{(equation 2)}$$

Equation 1 may represent an example sigmoid function configured to be used as an activation function. Equation 2 may represent an example rectified linear unit (ReLU) function configured to be used as an activation function. The layer of the DNN may select one or the two equations via a tuning parameter. If the activation function is selected via the tuning parameter, then both the activation functions may be tried and the function with the least amount of error may be selected. Additionally or alternatively, the activation function may be selected based on a network depth and/or a vanishing gradient problem. As known by those skilled in the art, the vanishing gradient problem may refer to a difficulty which arises when a network is trying to learn and/or tune earlier layers of the network. Thus, the DNN demands that each of its neural layers learn a single activation function, resulting in an increasing number of layers as the intricacy of the concept desired to learn increases, which may result in reduce processing speeds and efficiencies.

The ReLU function may be approximated by integrating equation 1, especially if learned weights, w, on the inputs of the neuron (e.g., $t=w^T x$) are large enough, then the integration may be:

$$y(t) = \max(0, t) \simeq \int_{\infty}^{t} \frac{1}{1+e^{-z}}\, dz; \qquad \text{(equation 3)}$$

Equivalently, y(t) may be a solution of the following first order linear differential equation:

$$y'(t) = \frac{1}{1+e^{-t}} ; \qquad \text{(equation 4)}$$

Thus, if each neuron, of the differential equations network 200, is configured to learn individually (e.g., learning the activation function needed, which may be different than activation functions learned by other neurons in the same layer), then a size of the differential equations network 200 may be smaller than the DNN while having a greater computing power. Said another way, each neuron in a layer (e.g., hidden layer 204) may be configured to learn independently of other neurons in the same layer. As such, a neuron may learn via the sigmoid activation function and another neuron may learn via a different variant of the sigmoid activation function, the ReLU activation function, or the like. In this way, an error between a predicted output of the differential equations network and an actual result (e.g., a desired output) may be reduced relative to a predicted output from a DNN. As such, the activation function needed, which may be different than other activation functions learned by other neurons within a shared hidden neural layer of the differential equations network, may be selected based on error reduction.

In one example, the differential equations network may be provided with real-world outputs, the real-world outputs representing outputs desired by a user from the differential equations network. Herein, real-world outputs may be referred to as actual outputs and predictions from the differential equations network may be referred to as predicted outputs. By providing the actual outputs to the differential equations network, the activation functions learned by the neurons of the single hidden neural layer may be adjusted to decrease an error and/or a difference between the predicted output and the actual output. In this way, for conditions where the actual output is unknown, confidence in the predicted output of the differential equations network may be higher than if error was not reduced.

To achieve this neural functionality while maintaining complex problem solving capabilities, a second order linear differential equation parameterized by three coefficients is shown in equation 5 below:

$$Ay''(t) + By'(t) + Cy(t) = u(t) = \begin{cases} 0 & t < 0 \\ 1 & t \geq 0 \end{cases} \approx \frac{1}{1+e^{-t}};$$ (equation 5)

A solution of the equation 5 may represent the activation function of each neuron. Equation 5 may capture oscillatory forms and may encompass common activation functions.

The differential equations network 200 may enable individual neurons to learn their own activation function based on their position in the network. For each neuron, the parameters A, B, and C along with input weights to a neuron may be learned. For example, if A=B=0, and C=1, then the neuron may choose the sigmoid as its activation function. As another example, if A=C=0 and B=1, then the neuron may choose an approximation of ReLU as its activation function. Thus, in one example, a neuron of the differential equations network 200 may mimic the behavior of common activation functions, such as sigmoid and ReLU. However, it will be appreciated by those of ordinary skill in the art that many other forms of activation functions may be learned by one or more neurons in the differential equations network 200 to represent a desired functionality in a condensed form without departing from the scope of the present disclosure. In this way, differential equations for nonlinear regression may be implemented for machine learning.

To learn the parameters of equations 5 (e.g., A, B, and C) and weights, w, and initial conditions C1 and C2, differential equation 5 is solved parametrically and the derivative of the solution with respect to input values to each neuron t and parameters A, B, C, C1, and C2. Parameters may be updated using an Adam update in a manner known to those skilled in the art.

In one example, first and second and further derivatives of the activation functions may be computed and/or calculated in a closed form. The closed form, which may be an algorithm, may be a stand-along component configured to work with existing deep learning technologies utilizing backpropagation for learning network parameters. By this abstraction, the algorithm may allow parameter learning by using Adam algorithm, which is a state-of-the-art method in the field. Usage of a forward approximation may be avoided via the Adam algorithm and may further facilitate imbedding the activation function in a plurality of modern neural network structures including but not limited to LSTM, CNN, MLP and the like as well as being capable of using many parameter learning and/or updating methods such as simple SGD, MSProp, Adam, AdaGrad, and the like.

Additionally or alternatively, the differential equations network 200 may include customized regularization functions and may utilize adversarial training methods.

In one example, the differential equations network 200 described above may learn one or more of the activation functions described below with respect to FIGS. 4A through 5E to predict a healthcare outcome. As an example, if the healthcare outcome to be predicted is associated with type-II diabetes, then the activation functions may be selected based on data gathered for diet, weight, blood sugar, age, gender, and the like. Thus, for the hidden layer 204, which is shown having four neurons, each neuron may learn its own activation function independent of the other neurons within the hidden layer 204 such that the differential equations network 204 may learn up to four different activation functions. This may allow the differential equations network to predict symptoms and responses in people with type-II diabetes or predict those most at risk for type-II diabetes. It will be appreciated that type-II diabetes is merely one example of a multitude of healthcare outcomes for which the differential equations system 200 may predict.

Turning now to FIGS. 3A and 3B, they show plots 300 and 350, respectively, which illustrate a strict $L_1$ regularization of a differential equation activation function. The plots may be based on results from the follow three function classes:

$$Ay'(t)+By(t)=C\sigma(t);$$ (class I)

$$Ay''(t)+By(t)=C\sigma(t);$$ (class II)

$$Ay''(t)+By'(t)=C\sigma(t);$$ (class III)

As such, plot 300 may represent a sigmoid function when classes I and II have A=0, B=1, C=0. Plot 350 may represent a ReLU function of an activation function of class 1 when A=1, B=0, and C=1. This may also be achieved by a class III function when A=0, B=1, and C=1.

Thus, FIGS. 3A and 3B illustrate common activation functions utilized by neural layers of previous examples. As described above, the previous examples may devote an entire hidden layer and all of the neurons therein to learn a single activation function. This may limit the number of possible activation functions that may be learned by the neural network or reduce a neural network efficiency while increasing a cost of maintenance of the neural network.

In one example, the differential equations network described above with respect to FIG. 2 and as will be described below in greater detail may be a compact network, smaller than previous examples of traditional neural networks, such as the DNN described above. The differential equations network may be more compact due to its ability to correlate data received by the input layers to a plurality of activation functions, where a desired number of activation functions are provided to a single hidden neural layer. The single, hidden neural layer may comprise a number of neurons equal to a number of activations functions of the plurality of activation functions. Each individual neuron of the single hidden neural layer may learn a different activation function, despite being within the single hidden neural layer. The individual neurons may work in tandem to provide an output to an output layer. Thus, the compact differential equations network may comprise only three layers while learning more than one activation function. The robustness of the compact differential equations network purchases increased efficiency and faster processing speed compared to deep neural network which need more than one neural layer if they are to learn more than one activation function.

Turning now to FIGS. 4A through 4J, they depict the flexibility and robustness of a differential equations network (e.g., differential equations network 200 of FIG. 2). This may be accomplished by allowing the parameters A, B, and C to assume a smaller number of potential values, a range of functions which can mimic the behavior of common activation functions as well other, new functions may be obtained. FIGS. 4A through 4J depict a range of activation functions obtained when parameters A, B, and C are restricted to values in the set S={0, 1, 2, 3, 4}. Said another way, activation functions shown in FIGS. 4A through 4J may depict different solutions to equation 5, the solutions configured to be learned by neurons of the differential equations network 200 of FIG. 2.

Figure 4A:
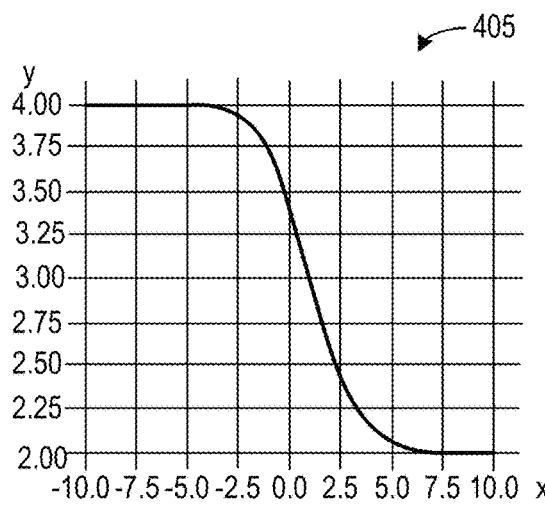

Specifically, FIG. 4A shows a plot 405 illustrating an activation function when:

$$y'(t) + y(t) = \frac{2}{1 + e^{(-t)}};$$

As shown, this activation function results in plot 405 to decrease from a maximum of y=4 to a minimum of y=2. Specifically, the plot 405 begins to decrease from y=4 at similar to x=−3 and continues to decrease until x=8. A rate of decrease may be greatest at x=1.

FIG. 4B shows a plot 410 illustrating an activation function when:

$$y'(t) + 3y(t) = \frac{4}{1 + e^{(-t)}};$$

As shown, this activation function results in plot 410 to increase from a minimum of y=0 to a maximum of similar to y=1.3. Specifically, the plot 410 begins to increase when x=−6 and stops increasing at similar to x=5. A rate of increase may be greatest when x=0.

Figure 4C:
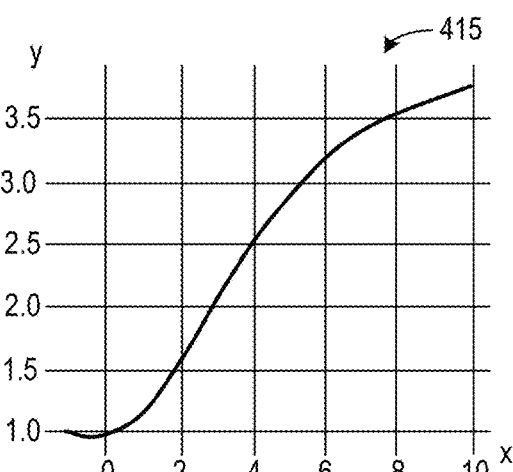

FIG. 4C shows a plot 415 illustrating an activation function when:

$$3y'(t) + y(t) = \frac{4}{1 + e^{(-t)}};$$

In the period shown, the activation function results in the plot 415 increasing from a minimum of similar to y=1 to a value of greater than y=3.5. Specifically, the plot 415 slightly decreases prior to x=0 before increasing at x=0.

Figure 4D:
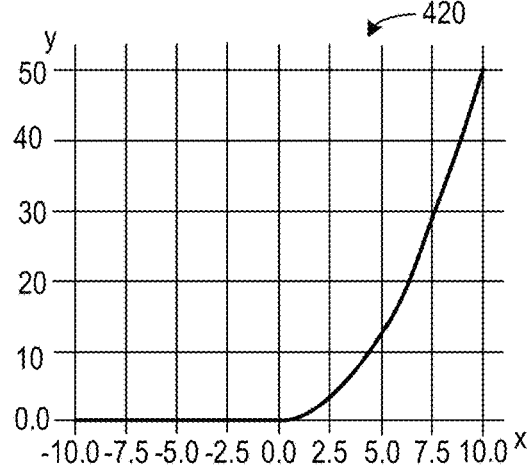

FIG. 4D shows a plot 420 illustrating an activation function when:

$$y''(t) = \frac{1}{1 + e^{(-t)}};$$

In the period shown, the plot 420 increases from a minimum of about y=0 passed a value of y=50. The plot 420 is substantially constant until x=1, where the plot 420 begins to increase following x=1.

Figure 4E:
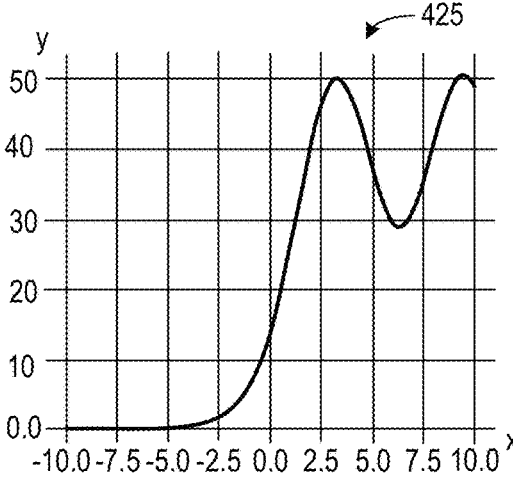

FIG. 4E shows a plot 425 illustrating an activation function when:

$$y''(t) + y(t) = \frac{2}{1 + e^{(-t)}};$$

As shown, the plot 425 begins to increase at near x=−2.5 from about y=0 to y=2.5. Upon reaching y=2.5, the plot 425 oscillates from y=2.5 to y=1.5 for values of x greater than about 3.

Figure 4F:
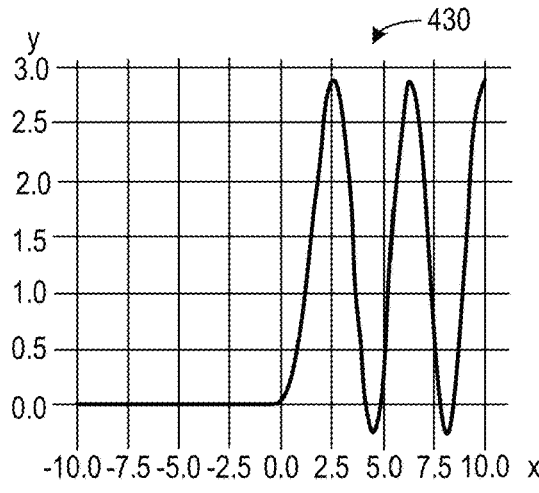

FIG. 4F shows a plot 430 illustrating an activation energy when:

$$y''(t) + 3y(t) = \frac{4}{1 + e^{(-t)}};$$

As shown, the plot 430 is substantially equal to y=0 for values of x less than about 0. At about x=0, the plot 430 increases toward about y=2.8. The plot 430 then oscillates between y=2.8 and y=−0.25 in the positive x-direction after y=2.5.

Figure 4G:
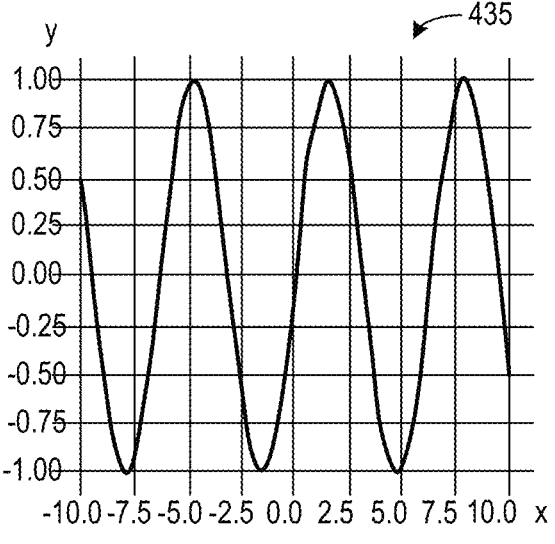

FIG. 4G shows a plot 435 illustrating an activation energy when:

$$3y''(t) + y(t) = \frac{4}{1 + e^{(-t)}};$$

As shown, this activation function results in plot 435 to undulate between magnitudes of positive y=1 and y=−1.

Figure 4H:
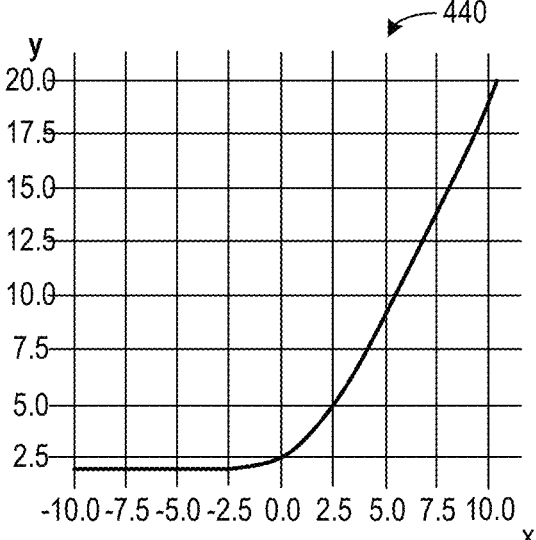

FIG. 4H shows a plot 440 illustrating an activation energy when:

$$y''(t) + y'(t) = \frac{2}{1 + e^{(-t)}};$$

As shown, the plot 440 is equal to a value less than 2y=0.5 for x-values less than 0. At near x=0, the plot 440 begins to increase and continues to increase for x-values in the positive direction to a value of about y=20.

Figure 4I:
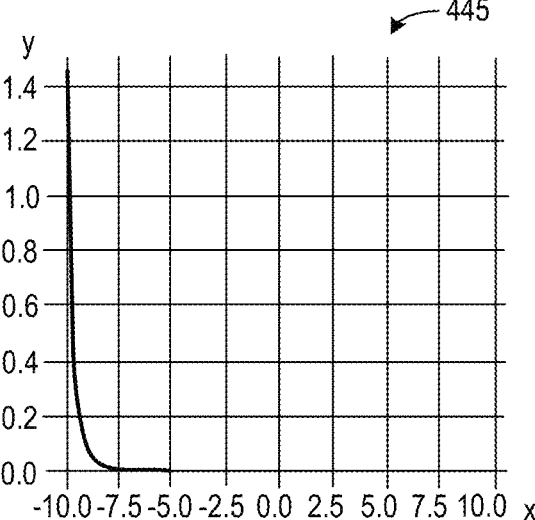

FIG. 4I shows a plot 445 illustrating an activation energy when:

$$y''(t) + 3y'(t) = \frac{4}{1 + e^{(-t)}};$$

As shown, the plot 445 decreases from y=1.4 to about y=0 and from x=−10 to similar to x=−8.8. For values of x greater than −8.8, the plot 445 is substantially equal to y=0.

Figure 4J:
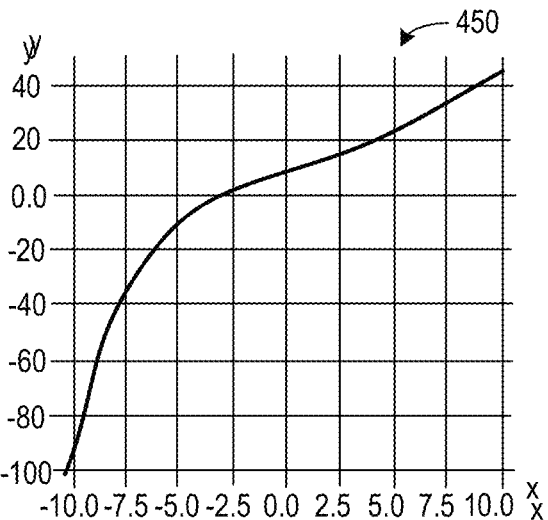

FIG. 4J shows a plot 450 illustrating an activation energy when:

$$3y''(t) + y(t) = \frac{4}{1 + e^{(-t)}}; \text{ and/or}$$

$$y''(t) = \frac{1}{1 + e^{(-t)}};$$

As shown, the plot 450 increases in the positive X-direction, where the plot 450 increases from −100 to positive 40. A rate of increase is faster between x=−10 to x=−5 than a rate of increase for values of x greater than −5. The plot 450 crosses 0 at x=−2.5.

FIGS. 5A to 5D, they show learning activation functions which may demand a Gauss Hypergeometric function (e.g., $_2F_1$(a, b; c; z)), which may be defined by the hypergeometric series. FIG. 5E shows a polylogarithm $Li_2$ (t), which may be defined as a power series. The Gauss Hypergeometric function is the solution of a second order linear differential equation. For efficiency, approximating these functions in determining an activation function may provide simpler functions which may reduce computing power demanded and time. Thus, the differential equations network 200, which may be configured to allow each neuron to learn one of the functions of FIGS. 5A through 5E, may spend less time solving a complex problem than a DNN. Approximations of $_2F_1$(a, b; c; z) for several a, b, and c values are shown in FIGS. 5A, 5B, 5C, and 5D.

Figure 5A:
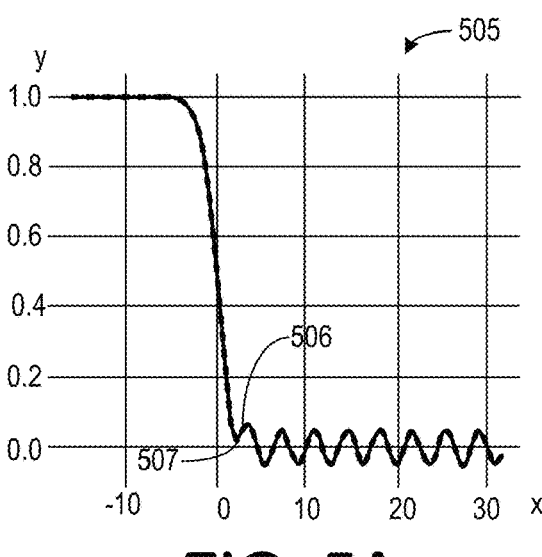
FIGS. 5A, 5B, 5C, 5D, and 5E show approximations of a Gauss Hypergeometric function and a polylogarithm of an activation function.

FIG. 5A shows a plot 505 illustrating an approximation of a real part of the following:

$$_2F_1(1,-\sqrt{3}j;1-\sqrt{3}j;-e^t);$$

This result may be the same for:

$$_2F_1(1,\sqrt{3}j;1+\sqrt{3}j;-e^t);$$

Since only the real part may be considered, and thus, the imaginary portions are ignored. This may be used to generalize for other approximations of $_2F_1$.

As shown, the plot 505 includes an actual plot 506 and an approximation plot 507, shown by solid and dashed lines, respectively. In one example, an accuracy of the approximation plot 507 increases as the approximation plot 507 overlaps with a greater amount of the actual plot 506. As such, portions of the actual plot 506 which are unseen may be occluded by the approximation plot 507. Both the actual 506 and the approximation 507 plots are substantially equal to 1 for values of x less than −3. At x=−3, the plots begin to decrease to 0.1, where the plots oscillate between 0.1 and −0.1 for values of x greater than 5.

Figure 5B:
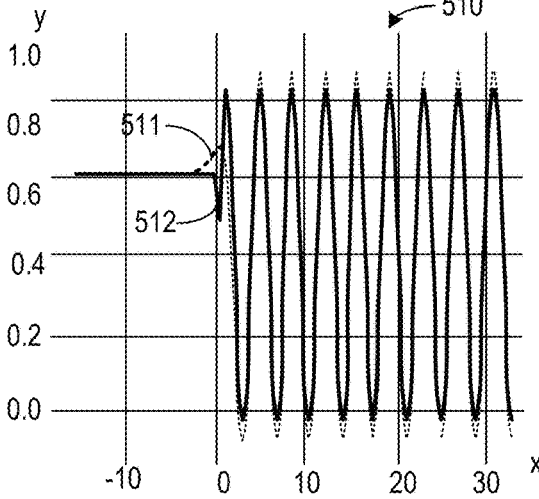

FIG. 5B shows a plot 510 illustrating an approximation of a real part of the following:

$$_2F_1(1,-\sqrt{3}j;1+\sqrt{3}j;-e^t);$$

As shown, the plot 510 comprises an actual plot 511 and an approximation plot 512, shown by dashed and solid lines, respectively. Similar to FIG. 5A, the accuracy of the approximation plot 512 increases as an overlap between the actual plot 511 and the approximation plot 512 increases. Thus, portions of the actual plot 511 may be occluded by the approximation plot 512.

Both plots are substantially equal to 1 for values of x less than −2. At similar to x=−2, the actual plot 511 increases toward y=2 before decreasing toward y=−2. However, the approximation plot 512 decreases toward y=0.5 at about x=−2. The approximation plot 512 may begin to correct itself and increase toward y=2, however, this may occur once the actual plot 511 begins to decrease (at similar to x=0). The approximation plot 512 then begins to decrease as the actual plot 511 approaches its minimum value (e.g., y=−2.3). The actual plot 511 and the approximation plot 512 may oscillate in tandem between y=−2.3 to y=2.3 for values of x greater than 2.

Figure 5C:
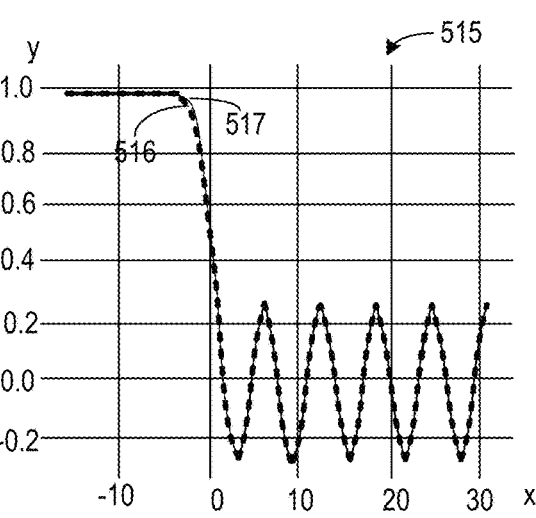

FIG. 5C shows a plot 515 illustrating an approximation of a real part of the following:

$$_2F_1(1,j,1+j,-e^t);$$

As shown, the plot 515 comprises an actual plot 516 and an approximation plot 517, shown by dashed and solid lines, respectively. Similar to FIG. 5A, the accuracy of the approximation plot 517 increases as the overlap between the actual plot 516 and the approximation plot 517 increases. Thus, portions of the actual plot 516 may be occluded by the approximation plot 517.

Both plots are substantially equal to y=1 for values of x less than approximately −2. At about x=−2, the actual 516 and the approximation 517 plots begin to decrease in tandem to y=−0.25. For values of x greater than 2, the actual 516 and approximation 517 plots oscillate between y=−0.25 and y=0.25.

Figure 5D:
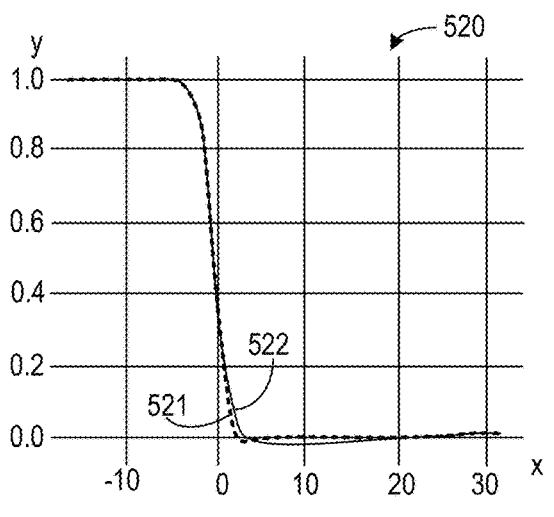
Figure 5E:
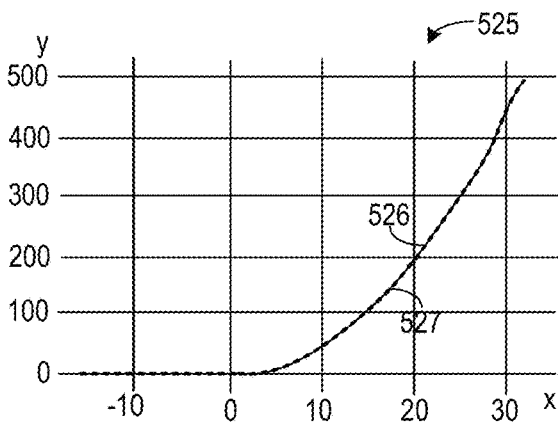

FIG. 5D shows a plot 520 illustrating an approximation of a real part of the following:

$$_2F_1(1,j,1+j,-e^t);$$

As shown, the plot 520 comprises an actual plot 521 and an approximation plot 522, shown by dashed and solid lines respectively. Similar to FIG. 5A, the accuracy of the approximation plot 522 increases as the overlap between the actual plot 521 and the approximation plot 522 increases. Thus, portions of the actual plot 521 may be occluded by the approximation plot 522.

Both plots are substantially equal to y=1 for values of x less than approximately −2. At about x=−2, the actual 516 and the approximation 517 plots begin to decrease in tandem to y=0. The plots remain substantially equal to y=0 for values of x greater than 1.

Turning now to FIG. 5E, it shows a plot 525 illustrating an approximation of a real part of the polylogarithm $Li_2$(t). As shown, the plot 525 comprises an actual plot 526 and an approximation plot 527 shown by dashed and solid lines, respectively. Similar to the FIGS. 5A, 5B, 5C, and 5D, the accuracy of the approximation plot 527 increases as an overlap between the actual plot 526 and the approximation plot 527 increases. Thus, portions of the actual plot 526 may be occluded by the approximation plot 527.

Both plots are substantially equal to y=0 for values of x less than 0. At x=0, both plots may begin to increase from y=0 to greater than y=500. As shown, the approximation plot 527 occludes a majority, if not all, of the actual plot 526.

Some exemplary problems which may be solved by one or more of the activation functions of FIGS. 4A through 5E. Some examples may include problems where the outputs include periodicity (e.g., chronic conditions, such as diabetes), problems where the outputs involve decay (e.g., patient gets progressively healthier or less healthy), problems where the outputs include rapid increase, where the rapid increase is super linear, quadratic, or exponential (e.g., anesthesia during surgery), and combinations thereof (e.g., chemotherapy).

An example of the differential equations network (e.g., differential equations network 200) learning activation functions may include solving problems where the outputs involve periodicity related to exacerbation for chronic obstructive pulmonary disease (COPD). A variety of patient factors may be measured, including but not limited to one or more of age, weight, medications, geographic location, diet, quantity and/or color of phlegm, and daily habits. These patient factors may be received by input neurons of the differential equations network, which may result inn number of activation functions being learned by n neurons of a hidden neural layer. The activation functions learned may be continuously adjusted to predict patient outcomes (e.g., exacerbation of COPD).

An example of the differential equations network (e.g., differential equations network 200) learning activation functions may include solving problems where the outputs involve periodicity related to glucose testing for diabetes. A variety of patient factors may be measured, including but not limited to one or more of age, weight, medications, geographic location, diet, blood sugar, and daily habits. These patient factors may be received by input neurons of the differential equations network, which may result inn number of activation functions being learned by n neurons of a hidden neural layer. The activation functions learned may be continuously adjusted to predict patient outcomes (e.g., glucose testing for diabetes).

An example of the differential equations network (e.g., differential equations network 200) learning activation functions may include solving problems where the outputs involve periodicity related to drug refill patterns. A variety of patient factors may be measured, including but not limited to one or more of age, weight, medications, geographic location, diet, schedule, and daily habits. These patient factors may be received by input neurons of the differential equations network, which may result in n number of activation functions being learned by n neurons of a hidden neural layer. The activation functions learned may be continuously adjusted to predict patient outcomes (e.g., drug refill patterns). In this way, the differential equations network may be used to prevent drug abuse and/or ensure drugs are taken to their prescribed dosing.

An example of the differential equations network (e.g., differential equations network 200) learning activation functions may include solving problems where the outputs involve decay related to acute conditions expected to get better over time (e.g., a respiratory infection). A variety of patient factors may be measured, including but not limited to one or more of age, weight, medications, geographic location, diet, quantity and/or color of phlegm, and daily habits. These patient factors may be received by input neurons of the differential equations network, which may result inn number of activation functions being learned by n neurons of a hidden neural layer. The activation functions learned may be continuously adjusted to predict patient outcomes.

An example of the differential equations network (e.g., differential equations network 200) learning activation functions may include solving problems where the outputs involve decay related to a patient having cancer and currently undergoing a successful course of treatment (e.g., cancer tumor size is decreasing). A variety of patient factors may be measured, including but not limited to one or more of age, weight, medications, geographic location, diet, tumor size, and daily habits. These patient factors may be received by input neurons of the differential equations network, which may result in n number of activation functions being learned by n neurons of a hidden neural layer. The activation functions learned may be continuously adjusted to predict patient outcomes (e.g., tumor remission to less than a threshold, where the threshold is based on a tumor size where the patient may stop treatment).

An example of the differential equations network (e.g., differential equations network 200) learning activation functions may include solving problems where the outputs involve decay related to healthiness indices that may decay over time (e.g., due to aging). A variety of patient factors may be measured, including but not limited to one or more of age, weight, medications, geographic location, diet, family history, and daily habits. These patient factors may be received by input neurons of the differential equations network, which may result in n number of activation functions being learned by n neurons of a hidden neural layer. The activation functions learned may be continuously adjusted to predict patient outcomes (e.g., Alzheimer's).

In some examples, additionally or alternatively, a plurality of activation functions from the one or more input neurons may be related to one or more healthcare parameters including age, weight, medications, geographic location, diet, current health status, and daily habits. The input neurons from the input layer may relay the plurality of activation functions to the neurons of the hidden neural layer, wherein each neuron of the hidden neural layer may learn a different activation function associated with one or more of the healthcare parameters. The neurons of the hidden neural layer may predict healthcare outcomes for one or more of diabetes, acute respiratory disorder, autoimmune diseases, autocrine diseases, neural diseases, mental health disorder, and cancers may combine outputs of one or more of the neurons of the hidden neural layer. As the healthcare parameters change over time, the plurality of activation functions may be adjusted.

An example of the differential equations network (e.g., differential equations network 200) learning activation functions may include solving problems where the outputs involve rapid increase related to cancer with an unsuccessful course of treatment. A variety of patient factors may be measured, including but not limited to one or more of age, weight, medications, geographic location, diet, type of cancer, tumor size, and daily habits. These patient factors may be received by input neurons of the differential equations network, which may result in n number of activation functions being learned by n neurons of a hidden neural layer. The activation functions learned may be continuously adjusted to predict patient outcomes. In this way, other cancer treatments may be prescribed based on the predicted output of the hidden neural layers.

An example of the differential equations network (e.g., differential equations network 200) learning activation functions may include solving problems where the outputs involve rapid increase related to situations comprising vital near-term predictions (e.g., patient risk assessment while in a coma). A variety of patient factors may be measured, including but not limited to one or more of age, weight, medications, geographic location, diet, duration of coma, cause of coma (e.g., medically induced or non-medically induced), and daily habits. These patient factors may be received by input neurons of the differential equations network, which may result in n number of activation functions being learned by n neurons of a hidden neural layer. The activation functions learned may be continuously adjusted to predict patient outcomes (e.g., risk of moving patient in a coma or the like). An example of the differential equations network predicting healthcare outcomes and providing one or more healthcare strategies for a patient is shown in FIG. 12.

An example of the differential equations network (e.g., differential equations network 200) learning activation functions may include solving problems where the outputs involve combinations of the above. For example, chemotherapy may cause unstable results initially, which may eventually taper-off and stabilize to a beneficial state. A variety of patient factors may be measured, including but not limited to one or more of age, weight, medications, geographic location, diet, type of cancer, white blood cell count, and daily habits. These patient factors may be received by input neurons of the differential equations network, which may result in n number of activation functions being learned by n neurons of a hidden neural layer. The activation functions learned may be continuously adjusted to predict patient outcomes.

In one example, the differential equations network may be provided with real-world outputs, the real-world outputs representing outputs desired by a user from the differential equations network. Herein, real-world outputs may be referred to as actual outputs and predictions from the differential equations network may be referred to as predicted outputs. By providing the actual outputs to the differential equations network, the activation functions learned by the neurons of the single hidden neural layer may be adjusted to decrease an error and/or a different between the predicted output and the actual output. In this way, for conditions where the actual output is unknown, confidence in the predicted output of the differential equations network may be higher than if error was not reduced.

Turning now to FIGS. 6A and 6B, they show plots 600 and 650, respectively, which illustrate a comparison between feed-forward neural network (FFNN) and a differential equations network. As such, the plot 600 may illustrate a fixed activation FFNN approximation with a single hidden layer comprising at least 10 neurons. The fixed activation FFNN uses Tesorflow with fixed sigmoid activations, in one example. The plot 650 may illustrate the differential equations network (e.g., differential equations network 200 of FIG. 2) comprising a single hidden layer comprising exactly three neurons, in the example of FIG. 6B.

As shown, the plots 600 and 650 both include actual plots 610 and 660, respectively. In one example, the actual plots 610 and 660 are substantially identical, having identical maxima and minimum values. In one example, the actual plots 610 and 660 are based on the following function:

$$f(x, w) = \frac{\sin(x) + 1}{2};$$ (function 1)

The function 1 may be based on data gathered regarding a healthcare outcome or some other outcome. As such, the function 1 may represent a data set. As such, activation functions may be supplied to the FFNN and the differential equations network to attempt to predict and/or simulate the function 1. By doing this, the FFNN and the differential equations network may be used to predict values of future inputs for the data set.

Plot 600 further comprises a predicted plot 620, which attempts to replicate the results of the actual plot 610. Likewise, plot 650 comprises a predicted plot 670, which attempts to replicate the results of the actual plot 660. An increase in overlap between the actual plot and the predicted plot may relate to the predicted plot being more accurate. As shown, the predicted plot 670, shown by a solid line, overlaps with the actual plot 660, shown by a dashed line, more than the predicted plot 620, shown by a solid line, overlaps with the actual plot 610, shown by a dashed line. As such, an error of the predicted plot 620 of the fixed activation FFNN may be greater than an error of the predicted plot 670 of the differential equations network, despite the FFNN comprising a greater number of neurons than the differential equations network. In one example, an error of the fixed activation FFNN is 0.00027 and an error of the differential equations network is $1e^{-6}$. Additionally, a computing efficiency of the differential equations network may be higher than an efficiency of the FFNN. For example, the size of the differential equations network is smaller, demands less storage space, and consumes less power and processes faster to predict the function 1 more accurately than the FFNN.

Turning now to FIGS. 7A, 7B, and 7C, they show plots 700, 725, and 750, respectively. Plot 700 comprises an actual plot 705, shown by a dashed line, plot 725 comprises an actual plot 730, shown by a dashed line, and plot 750 comprises an actual plot 755, shown by a dashed line. Each of the actual plots 705, 730, and 755 may be based on the following function:

$$f(x, w) = \frac{\sin(2x) + 1}{2};$$ (function 2)

In this way, each of the actual plots 705, 730, and 755 may be substantially identical and based on the function 2. Similar to the function 1, the function 2 may be based on data gathered to determine a healthcare outcome or the like.

Plot 700 further comprises a predicted plot 710, shown by a solid line, where the predicted plot 710 represents a fixed activation FFNN approximation comprising one hidden layer having 100 neurons. As shown, the predicted plot 710 overlaps with a small portion of the actual plot 705. As such, the plot 710 comprises an error of 0.0276.

Plot 725 further comprises a predicted plot 735, shown by a solid line, where the predicted plot 735 represents a fixed activation FFNN approximation comprising two hidden layers, each of the layers comprising 100 neurons. Thus, the fixed activation FFNN of plot 725 comprises 200 neurons total across its two layers. As shown, the overlap between the predicted plot 735 and the actual plot 730 is greater than an overlap between the predicted plot 710 and the actual plot 705 of FIG. 7A. Thus, the error of the predicted plot 735 is substantially equal to $4e^{-5}$.

Plot 750 further comprises a predicted plot 760, shown by a solid line, where the predicted plot 760 represents a differential equations network (e.g., differential equations network 200) comprising a single hidden layer having three neurons. In the example of FIG. 7C, the activation functions learned by the activation functions depicted with respect to FIGS. 4B, 4D, and 4E. As such, one of the three neurons may learn the activation function of FIG. 4B, a second of the three neurons may learn the activation function of FIG. 4D, and a third of the three neurons may learn the activation function of FIG. 4E. Thus, each of the three neurons of the single hidden layer may learn different activation functions, unlike the neurons of the fixed activation FFNNs of FIGS. 7A and 7B. An error of the differential equations network approximation is less than $1e^{-6}$. Thus, the predicted plot 760 overlaps with a greater portion of the actual plot 755 than the predicted plot 735 and actual plot 730 of FIG. 7B.

In this way, the differential equations network comprises fewer neurons than the fixed activation FFNNs while providing more accurate prediction models. All while demanding less storage space and parallel computing power. This may provide a cost savings to a user.

Turning now to FIGS. 8A and 8B, they show a comparison of a plot 800 of a differential equations network and a plot 850 of a neural network. Both plots 800 and 850 comprise actual plots 810 and 860, respectively, where the actual plots are based on a modified sine function, such as the function below.

$$f(x, w) = \frac{\sin x}{2} + 0.5;$$ (function 3)

The differential equations network and the neural network each comprise one or more neurons, the neurons of the network working in combination to predict the actual plots 810 and 860.

The plot 800 further comprises a predicted plot 820, which illustrates an output of the neurons of the differential equations network. In one example, the output is a combined output of the neurons. The combined output is based on the two neurons included in the differential equations network, where each of the neurons may learn the same or different activation functions, such as the activation functions described above. An error between the predicted plot 820 and the actual plot 810 is $7.90\times10^{-5}$.

The plot 850 further comprises a predicted plot 870, illustrating an output of the neurons of the neural network. The output is combined output based on an activation function learned by the 20 neurons of the neural network. In one example, each of the 20 neurons learns the same ReLU activation function, such as the function described with respect to FIG. 3B. An error between the predicted plot 870 and the actual plot 860 is 0.009, which is greater than the error between predicted plot 820 and actual plot 810. Thus, even though the neural network is an entire order of magnitude larger (e.g., 10 times larger), it is less accurate at predicting the actual plot than the differential equations network.

Turning now to FIGS. 9A, 9B, and 9C, they show plots 900, 930, and 960 respectively. The plot 900 depicts an actual plot 910 and predicted plot 920 of a differential equations network. The plot 930 depicts an actual plot 940 and a predicted plot 950 of a neural network. Lastly, plot 960 depicts an actual plot 970 and a predicted plot 980 of a neural network. In one example, each of the actual plots 910, 940, and 970 are exactly identical and based on the following:

$$f(x, w) = \sin 3x - \cos 4x^2 + \frac{4\left(\cos^{-1}\sin\frac{x}{4}\right)}{3};$$ (function 4)

The predicted plots 920, 950, and 980 attempt to mimic and/or simulate the actual plots 910, 940, and 970, respectively. The predicted plot 920 may be generated based on a combination of activation functions learned by the 15 neurons of the differential equations network of plot 900. The predicted plot 950 may be generated based on a ReLU activation function learned by the 100 neuron of the neural network of plot 930. The predicted plot 980 may be generated based on a ReLU activation function learned by the 100 neuron of the neural network of plot 960. An error between the predicted plot 920 and the actual plot 910 is 0.03. An error between the predicted plot 950 and the actual plot 940 is 0.075. An error between the predicted plot 980 and the actual plot 970 is 0.092. As such, the differential equations network provides the most accurate prediction of the function 4 while being more than six times smaller than the neural networks.

Turning now to FIG. 10, it shows a method 1000 a hidden neural network layer obtaining a plurality of activation functions from an input layer. Instructions for carrying out method 1000 and the rest of the methods included herein may be executed by a controller based on instructions stored on non-transitory memory of the controller.

The method 1000 begins at 1002 where the method 1000 may include a hidden neural network layer obtaining n activation functions from n input neurons. Each activation function of the n activation functions may be different. Additionally, the hidden neural network layer may be the hidden layer 204. In one example, the activation functions may be substantially similar to activation functions of FIGS. 4A through 5E.

At 1004, the method 1000 may include selecting which of the activation functions to teach n neurons of the neural layer. For example, a first neuron may learn a first activation function and a second neuron may learn a second activation function. In this way, neurons of a same layer (e.g., the hidden neural network layer) may learn different activation functions. In one example, there may be a greater number of activation functions than neurons. Thus, a number of n activation functions is greater than a number of n neurons. In another example, the numbers are exactly identical.

Turning now to FIG. 11, it shows a method 1100 illustrating selecting which of the activation functions neurons of the hidden neural network layer are to be learned.

The method 1100 begins at 1102 where the method 1100 may include receiving an output of the neural layer. In one example, the output may be substantially similar to a predicted output of FIGS. 6B, and 7C. As such, the output may be based on the activation functions learned at 1102 of method 1100. For example, if the first neuron learns the first activation function and the second neuron learns the second activation function, then the output may be based on a combination of the first and second activation functions.

At 1104, the method 1100 may include determining an error between the output and an expected value. The error may be based on a difference between the output and the expected value, wherein the error increases as the difference increases. In one example, the expected value is similar to an actual plot of FIGS. 6B and 7C.

At 1106, the method 1100 may include determining if the error is equal to a lowest achievable error. The lowest achievable error may be based on an error between the expected value and an output of the neurons of the hidden neural network layer closest to the expected value. In one example, the lowest achievable error is limited to the activation functions obtained by the hidden neural network layer.

If the error is the lowest achievable error, then the method 1100 proceeds to 1108 to maintain current operating parameters and does not change the activation functions learned by the neurons of the hidden neural network layer. However, if the error is not equal to the lowest achievable error (e.g., the error is greater than the lowest achievable error), then the method 1100 may proceed to 1110 to adjust one or more of the activation functions learned by n neurons of the hidden neural network layer. In one example, activation functions are adjusted one at a time. For example, an activation function of a first neuron may be adjusted, if the adjustment decreases the error, then the adjustment may be maintained and an activation function of a second neuron may be adjusted. If the adjustment of the second neuron increases the error, then the adjustment of the second neuron may be forgotten. This may proceed until the error is a lowest achievable error. That is to say, the activation function may be repeatedly adjusted until the lowest achievable error is reached. As such, errors values of activation functions adjusted differently may be compared to one another to determine the lowest achievable error. In some examples, additionally or alternatively, the lowest achievable error may be estimated based on previous adjustments to other similar activation functions. Once an activation function is adjusted so its error is within a threshold amount (e.g., 95% or more) of estimated lowest achievable error, then the adjustment may be maintained.

Turning now to FIG. 12, it shows a method 1200 for utilizing a differential equations network (e.g., differential equations network 200 of FIG. 2) to adjust a healthcare plan for a patient. The method 1200 begins at 1202, which may include providing data to the input layer regarding patient health. The input layer may be updated based on data input into a controller, wherein the controller may provide feedback to the input layer regarding an age, a gender, a weight, an activity level, a blood pressure, and other metrics regarding patient health status. In some examples, data provided may be directly associated with a current patient disease. For example, if the patient has type-II diabetes, then blood glucose data may be provided while other less pertinent data may be omitted. In some examples, additionally or alternatively, a plurality of patient health data may be provided regardless of a degree of relevance to a patient disease.

The method 1200 may proceed to 1204, which may include updating the hidden neural layer, such as hidden neural layer 204 of FIG. 2. Updating the hidden neural layer may include transmitting data to the hidden neural layer, wherein each neuron of the hidden neural layer may be assigned a different activation function based on data provided by the input layer. In one example, each data point provided by the input layer may be associated with its own activation function. As another example, some activation functions may encompass multiple data points, such that a single neuron learning an activation function may accurately predict outcomes and/or consequences for a plurality of patient health data. In some examples, activation functions already assigned to the neurons of the hidden neural layer may be updated, rather than adjusted to different activation functions. For example, coefficients and/or mathematical operators may be adjusted rather than learning a new activation function. In some examples, some neurons may learn new activation functions while activation functions of other neurons may be adjusted while a structure and/or a type of the activation function remains the same. By adjusting an activation function, its output may be adjusted in terms of magnitude (e.g., local maxima are adjusted, slope is adjusted, etc.) while a newly learned activation function may provide a different output than a previously learned activation function (e.g., logarithmic output versus an exponential output).

The method 1200 may proceed to 1206, which may include determining if an output layer prediction has changed. The output layer prediction may be based on a combination of one or more activation function predictions. The activation function predicts may predict a future patient health condition based on a transition from a previous health status to a current health status, current prescriptions, dose of current prescriptions, and the like.

If the output layer prediction has not changed, then the method 1200 may proceed to 1208, which may include maintaining a current healthcare plan for a patient. As such, the patient's medications and other current healthcare treatment options may be maintained.

If the output layer prediction has changed, then the method 1200 may proceed to 1210, which may include evaluating the prediction. Evaluating the prediction may include analyzing the prediction to determine if the predicted output is likely based on experience, if a current healthcare facility is capable of implementing the output layer prediction, and if the patient desires the healthcare plan changes.

The method 1200 may proceed to 1212 to adjust the healthcare plan for the patient. Adjusting the healthcare plan may include adjusting one or more of an amount and/or type of prescriptions and health services performed to the patient.

As one real-world example of the method 1200, a patient may suffer from high-blood pressure, wherein the patient may receive one or more drugs for controlling (e.g., decreasing) their blood pressure. If the patient suffers a stroke, which may decrease their blood pressure, then the input layer may be updated to include the stroke and other patient health factors (e.g., blood pressure). If the patient's blood pressure following the stroke is low, then the output layer prediction may change, wherein the change may include decreasing a dosage of or withholding drugs for controlling the patient's blood pressure.

As another real-world example of the method 1200, a patient may suffer from heart disease. As the disease progresses, one or more patient health factors may change, wherein the change may be used to update the input layer, which may result in changes to activation functions learned by neurons of the hidden neural layer. If the output layer prediction may include one or more changes, which may include a likelihood of one or more patient symptoms along with an updated healthcare plan to prevent or delay the patient symptoms. For example, if a heart attack is predicted, then the changes may include increasing a dosage of medication currently prescribed to decrease blockage to mitigate the likelihood of the heart attack. Additionally or alternatively, the output layer prediction may include one or more plans. For example, the output layer prediction may initial instruct the healthcare provider to increase the dosage of the medication. The output layer prediction may further advise surgery in the event that increasing the dosage does not sufficiently improve patient health factors to prevent and/or mitigate the likelihood of the heart attack.

As a further real-world example of the method 1200, a patient may suffer from cancer (e.g., a glioblastoma). The input layer may be updated based on a type of glioblastoma (e.g., methylated vs unmethylated), patient health outside of the glioblastoma (e.g., weight, blood pressure), etc. The hidden neural layer may be updated such that each neuron learns a different activation factor configured to predict one or more healthcare outcomes with a greatest degree of confidence. As the disease progresses, the output layer prediction may change due to changes to the activation functions of the hidden neural layer. For example, during the second or third recurrence of the cancer, the output layer prediction may provide two or more options, a first option including removal of a lobe of the brain and a second option including no action. A healthcare team may evaluate the two or more options and consult with the patient to determine which option to execute.

Turning now to FIG. 13, it shows a plurality of plots 1300, 1310, 1320, 1330, 1340, and 1350 each illustrating a different activation function. Lines 1301, 1311, 1321, 1331, 1341, and 1351 of plots 1300, 1310, 1320, 1330, 1340, and 1350, respectively, represent the activation functions and lines 1302, 1312, 1322, 1332, 1342, and 1352 of plots 1300, 1310, 1320, 1330, 1340, and 1350, respectively, represent derivatives with respect to t. Lines 1303, 1313, 1323, 1333, 1343, and 1353 of plots 1300, 1310, 1320, 1330, 1340, and 1350, respectively, represent derivatives, each of which may be a partial derivative, with respect to a. Lines 1304, 1314, 1324, 1334, 1344, and 1354 of plots 1300, 1310, 1320, 1330, 1340, and 1350, respectively, represent derivatives, each of which may be a partial derivative, with respect to b. Lines 1305, 1315, 1325, 1335, 1345, and 1355 of plots 1300, 1310,

1320, 1330, 1340, and 1350, respectively, represent derivatives, each of which may be a partial derivative, with respect to c. Note that lines 1303 and 1314 may be overlapped and obscured by lines 1305 and 1315, respectively. Plots 1300 and 1310 may be ReLU and ReQU activation functions respectively. The stepwise increase of the derivative with respect to t (line 1301) in plot 1300 may be an artifact of approximating a delta (e.g., Dirac's delta), which may be a derivative of a Heaviside step function. For plots 1300, 1310, 1320, 1330, and 1340, each of the activation function and its derivatives, whether with respect to t, a, b, and c, are each equal to 0 when x≤0.

Turning now to FIG. 14, shows plots 1400 and 1450 which illustrate a transformation of a ReLU activation function to a cosine activation function. Plot 1400 illustrates a ReLU activation function comprising solutions of the following equation:

$$ay''+by'+cy=u(t)$$

Plot 1450 illustrates a path an initialized activation function takes, such as the activation function of plot 1400, to gradually transform into a different one, such as transforming into a cosine activation function. Points of the plots 1400 are manipulated into and equivalently represent on a 5-dimensional space, 3-dimensions of which are shown in plot 1450.

In one example, plot 1400 illustrates solutions of its equation on a manifold of functions. Plot 1450 may equivalently represent every point of the manifold on a 5-dimensional space, where a path an initialized function takes to be gradually transformed to a different one is shown by the red arrow.

Turning now to FIG. 15, it shows plots 1500, 1520, 1540, and 1560. Plots 1500, 1520, and 1540 may represent fixed activation function neural networks (FFNNs) approximating a sine function. More specifically, plot 1500 may represent a ReLU fixed activation network comprising 10 neurons. Plot 1520 may represent a LeakyReLU fixed activation network comprising 10 neurons. Plot 1540 may represent a SELU fixed activation network comprising 10 neurons. Plot 1560 may represent a differential equations neural network, comprising only a single neuron in a single neural hidden layer, approximating the sine function. The differential equations neural network comprising the single neuron is more accurate than the 10 neurons of the fixed activation networks, which is shown by a difference in the test plots (lines 1503, 1523, 1543, and 1563 of plots 1500, 1520, 1540, and 1560, respectively) and the train plots (lines 1502, 1522, 1542, and 1562 of plots 1500, 1520, 1540, and 1560, respectively), and the actual sine plot (represented by lines 1501, 1521, 1541, and 1561 of plots 1500, 1520, 1540, and 1560, respectively), wherein more overlap between the test and train plots with the actual sine plot correlates to a greater accuracy. As shown in plot 1560, the test and train plots (lines 1563 and 1562, respectively) overlap with the actual sine plot for almost an entirety of the periods illustrated. Further, line 1562 may be overlapped and obscured by line 1561. A difference between the test and train plots may include different initializations. As shown in plot 1560, the differential equations network activation functions transformed during a training process into a sine-like solution to substantially match the sine function (line 1561).

Turning now to FIG. 16, it shows plots 1600, 1620, 1640, and 1660. Plots 1600, 1620, and 1640 may represent FFNNs approximating a sine function more complex than the sine function approximated in FIG. 15. As such, the FFNNs of plots 1600, 1620, and 1640 may need more neurons than the FFNNs of plots 1500, 1520, and 1540 of FIG. 15. More specifically, plot 1600 may represent a RELU fixed activation network comprising 250 neurons spread across one or more layers. Plot 1620 may represent a LeakyRELU fixed activation network comprising 250 neurons spread across one or more layers. Plot 1640 may represent a SELU fixed activation network comprising 250 neurons spread across one or more layers. Plot 1660 illustrates a differential equation network comprising 25 neurons arranged within a single neural layer. Lines 1602, 1622, 1642, and 1662 of plots 1600, 1620, 1640, and 1660, respectively, represent a predicted output of the respective network and lines 1601, 1621, 1641, and 1661 of plots 1600, 1620, 1640, and 1660, respectively, represent an actual value of the sine function. Note that line 1662 may be overlapped and obscured by line 1661. Thus, the fixed activation networks of produce outputs less accurate than the differential equation network despite having a network size comprising ten times more neurons. Thus, the fixed activation networks are less accurate while demanding a greater amount of storage space.

TABLE 1

| | Activation | | | | |
|---|---|---|---|---|---|
| | ReLU | LReLU | SELU | Swish | DifEN |
| Accuracy | 0.9891 | 0.9890 | 0.9903 | 0.9918 | 0.9919 |

The performance of a differential equations network (DifEN) with baselines was compared on a MNIST handwritten digit dataset. The other fixed activation convolutional layers neural networks were equipped with ReLU, LeakyReLU (LReLU), SELU, or Swish activation functions. The fixed activation networks used the same architecture, which included three convolutional layers consisting of 20 5×5 filters, 40 5×5 filters, and 60 4×4 filters, respectively. A pooling layer and a dropout layer were applied after the second and third activation layers, and two fully connect layers followed with 200 neurons in the first fully connected layer.

The differential equations network comprises two convolutional layers with 20 5×5 filters and 40 3×3 filters, respectively. One pooling and one dropout layer were applied after the second activation function. One fully connected layer was used in the first fully connected layer as opposed to the two used with the fixed activation networks. Dropout probability, batch size, epochs, and learning rate were similar across all networks. For these experiments, three-fold cross-validation was executed along with and the mean result for each network was reported. Thus, the comparison demonstrates the ability of the differential equations network to achieve network compression without sacrificing performance compared to the fixed activation networks. Results of a similar demonstration using the above described with diabetes regression data is shown in Table 2 below.

TABLE 2

| Size | DifEN | ReLU | LReLU | SeLU | Swish |
|---|---|---|---|---|---|
| 1 | 2490.781 | 7391.783 | 6977.1 | 6289.9 | 4298.493 |
| 2 | 2446.003 | 3759.527 | 4562.308 | 3793.336 | 3249.608 |
| 4 | 2412.504 | 2931.891 | 2720.555 | 2912.025 | 2839.323 |
| 8 | 2313.98 | 2465.16 | 2398.2 | 2488.361 | 2664.854 |
| 16 | 2117.47 | 2334.454 | 2357.557 | 2165.465 | 2236.137 |

Thus, table 2 shows a DifEN may perform equally or better than a network with over two times the number of parameters compared to a fixed activation network. Additionally, DifEN may learn better approximations compared to networks with fixed activations throughout.

In this way, the differential equations networks comprising one or more activation functions within a single neural layer demonstrate a capability of a differential equations network to learn complex concepts and/or functions while decreasing network size compared to fixed activation networks. By learning more accurate approximations with a smaller network, the differential equations network may be a good candidate for on-device applications and/or for devices with less computing power. For example, for a fixed activation network to approximate complex concepts, it may be deployed on a computer or other electronic device comprising a threshold amount of computing power. However, the differential equations network may be deployed on a computing device comprising less than the threshold amount of computing power. Thus, differential equations networks may circumvent memory and latency issues that plague fixed activation networks in space, robotics, healthcare, and other complex applications.

Turning now to FIG. 17, it shows plots 1700, 1720, and 1740, each plot representing a different activation function. In one example, FIG. 17 shows how changing a coefficient in a low dimensional differential equation space representation will affect the resulting function on the manifold. Each of the plots illustrate a different parameter of the activation function being varied, wherein an effect of the variation of the parameter on an output is plotted. For example, a parent equation may comprise three variables, namely variables a, b, and c. Plot 1700 may illustrate different outputs if a is adjusted while maintaining b and c constant (as represented by lines 1701, 1702, 1703, 1704, 1705, 1706, and 1707). Plot 1720 may illustrate different outputs of the parent equation if b is adjusted while maintaining a and c (as represented by lines 1721, 1722, 1723, 1724, 1725, 1726, and 1727). Plot 1740 may illustrate different outputs of the parent equation if c is adjusted while maintaining a and b (as represented by lines 1741, 1742, 1743, 1744, 1745, 1746, and 1747).

As an example, n input neurons from n dimensions of a differential equations network may provide n activation functions to n neurons of a single hidden neural network layer. The n neurons may provide a combined output (e.g., an average or a sum of the learned activation functions) attempting to mimic a desired output. In one example, the desired output is based on a function fitted to gathered data. As such, the combined output may attempt to predict and/or simulate the desired output without gathering further data points. A reliability of the combined output may be measured by an error determined between the combined output and the desired output. If the error is not a lowest error or is greater than a threshold error, then one or more activation functions learned by the n neurons of the hidden neural network layer may be adjusted, wherein the adjusting may include adjusting coefficients and/or other operators of the activation functions. In one example, the threshold error is a non-zero value and equal to 0.0001. It will be appreciated that the threshold error may be based on other values without departing from the scope of the present disclosure. At any rate, one or more activation functions of the n neurons may be adjusted to decrease the error of the combined output. Thus, different activation functions of the n activation functions may be learned by one or more of the n neurons. The activation functions learned may continue to be adjusted until the error is sufficiently low (e.g., below the threshold error or equal to a lowest possible error).

In some embodiments, additionally or alternatively, activation functions may be fixed in each layer of a network, and the choice of activation function may be either determined by tuning, or it is decided due to certain parameters (e.g., the depth of the network and the vanishing gradient problem). For example, one of the reasons for selecting the ReLU activations over the sigmoid is that ReLU may comprise a constant slope that does not fade away in deeper networks due to saturation. The solution of a calculus of variations problem is one, or a set of functions that can also be acquired by solving a corresponding differential equation obtained by the Euler-Lagrange equation. Neurons initialized by the ReLU activations may change their parameters to learn a function, which may allow the neurons to more accurately predict health outcomes. That is to say, ReLU activations may adapt over time to predict outcomes more accurately than a feed-forward neural network (FFNN).

FFNNs with monotonically-increasing activation functions may be universal approximators. Networks with radial basis activation functions that are bounded, increasing and then decreasing may also be universal approximators. The selection of activation functions may be considered a tuning parameter. Two utilitarian activation functions are the sigmoid, and the rectified linear unit (ReLU) functions, which are defined above. The ReLU function can be approximated by integrating the sigmoid function (e.g., if the learned weights w have a large magnitude and the sigmoid function is close to the step function). Utilization of the ReLU and sigmoid activation functions allows a differential equations network (DEN), such as the differential equations networks described above to comprise a lower number of neurons than the FFNN, thereby reducing an operating cost and increasing an accuracy of predicted outcomes.

If each neuron of a DEN may learn its own individual activation function, the network as a whole may have the flexibility to approximate complicated concepts with a significantly reduced number of neurons. Each hypothetical neuron may be capable of performing the tasks of a larger subset of the fixed activation neurons in a FFNN or other similar network where each layer of neurons comprises a single, fixed activation function. By allowing the neurons of a single layer to adapt and learn individually, while operating in harmony to predict outcomes more accurately, the DEN may experience improved results while demanding less memory to operate.

Thus, the activation function of each neuron may be characterized as the solution of a second order linear differential equation parametrized by five coefficients. And, if these coefficients are the only additional parameters that each neuron learns, then each neuron may learn its desired activation function independent of the other neurons. Additionally, this learning may be in conjunction with learning conducted by the other neurons such that the neuron may learn functions in which the other neurons are deficient. This formulation may address a few key difficulties, including a formulation that is simple, that can capture oscillatory forms, and that includes approximations of common activation functions such as ReLU and sigmoid. Given these constraints, equation 5 above, operating as a second order linear differential equation may meet the above guidelines, as one example.

For fixed a, b, and c, the solution of this differential equation will be $y=f(t)$ for some function f that lies in an affine space, parametrized by two parameters c1 and c2 that represent the initial conditions of the solution. Using only the real part of the solution if it yields a complex function.

By using a step function, complex-valued solutions may be avoided that involve special mathematical functions such as the Gauss hypergeometric, Li2, and Bessel functions. However, these functions may be approximated for the resulting non-homogenous solutions if desired.

With this setting, if $a=0$, $b=0$, and $c=1$, the sigmoid function may be calculated. If $a=0$, $b=1$, and $c=0$, the ReLU function may be calculated. If $a=1$, $b=0$, and $c=0$, a rectified quadratic form $y=ReLU(t)2+c_1t+c_2$, may be calculated, which is the solution of $y''(t)=u(t)$. If $b2-4ac<0$, at least some oscillatory behaviors may be observed, which may be decaying, and on the limiting case, if $b=0$ and $a$; $b>0$, the frequency of oscillation may be $w=\sqrt{a/c}$. To regulate the behavior of the functions $a$; $b$; $c\in[0; 1]$, and $c_1$; $c_2 \in[-1; 1]$ are limited. The abovementioned cases are merely examples of solutions that could be chosen, but it will be appreciated by those of ordinary skill in that art the extensive range of functions that can be generated by varying these few parameters.

To learn the parameters $\theta=[a; b; c; c_1; c_2]^T$ along with weights w on input values to each neuron, a coordinate descent algorithm may be utilized. Both weights w and $\theta$ are learned using the conventional backpropagation algorithm. The differential equation solution, with respect to a given neuron, is used as that neurons activation function. Note that these activation functions can be obtained using ordinary differential equation (ODE) integrators, or via closed-form solutions. The closed-form solutions, and derivative with respect to the variable parameter t (i.e., the input to the activation function), $c_1$ and $c_2$ may be derived parametrically.

For parameters a, b, c, the derivative is approximated by fixing two of the parameters, and perturbing the other by a value $\Delta$. The approximate derivative for the parameter a may be the difference between the solution of the ODE $(a+\Delta)y''(t)+by'(t)+cy(t)=g(t)$, and $ay''(t)+by'(t)+cy(t)=g(t)$ divided by $\Delta$. The approximate derivative for b and c may be obtained in a similar fashion. These approximate derivatives may reduce the loss function, particularly when they are used with the RMSProp or Adam optimization algorithms. The values of a, b, and c are discretized and pre-computed closed-form derivations for the solution activation functions and their derivatives. In the learning process, a; b; c; $c_1$ and $c_2$ are treated like biases and their values updated based on the direction of the corresponding gradients in each mini-batch.

The solution of a differential equation may be different when the desired initial conditions change. In the algorithm for determining the derivative of the solutions with respect to their coefficients, the initial condition of the solutions of the perturbed equations may be fixed to have the exact initial conditions that solutions should have had before perturbation. In particular, if y(t) is the solution of the original differential equation, and y $\Delta$(t) is the solution of the perturbed equation, it may be desired to determine that both the function and its derivative have the same values at the origin.

In this way, a differential equations network may comprise fewer neurons than a fixed activation FFNN while providing greater or equal problem solving capabilities then the fixed activation FFNN. This may be achieved by allowing each neuron of the differential equations network to learn independently of other neuron within a same layer. The technical effect of allowing neurons to learn independently is to allow a first neuron to learn a first activation function and a second neuron to learn a second activation function, different at the first, such that the differential equations network demands less memory space and less parallel computing power than the fixed activation FFNN. By doing this, the differential equations network may be more efficient, faster, and smaller than the fixed activation FFNN.

An embodiment of a method for performing differential equations network (DEN) computations for a DEN having a plurality of DEN layers, the method comprising obtaining, from n input neurons along n dimensions of the DEN, n activation functions for n neurons of a hidden neural network layer of the DEN, selecting an activation function of the n activation functions to teach to a neuron of the n neurons, where each neuron of the n neurons learns a different one of the n activation functions to provide a compact DEN, and predicting an outcome based on a combination of learned activation functions. A first example of the method further includes where hidden neural network layer is a single neural layer comprising each of the n neurons, and where there are no other layers in the compact DEN other than an input layer, the hidden neural network layer, and an output layer. A second example of the method, optionally including the first example, further includes where the n neurons are configured to learn activation functions independently of one another. A third example of the method, optionally including the first and/or second examples, further includes where the selecting is based on at least an error between an actual value and the outcome, where the outcome is based on activation functions learned by each of the n neurons. A fourth example of the method, optionally including one or more of the first through third examples, further includes where the n neurons of the hidden neural network layer learn activation functions to decrease the error. A fifth example of the method, optionally including one or more of first through fourth examples, further includes where the n neurons comprise at least a first neuron which learns a first activation function and a second neuron which learns a second activation function, wherein the first activation is different than the second activation function. A sixth example of the method, optionally including one or more of the first through fifth examples, further includes where decreasing an error of the outcome determined by the first and second neurons via adjusting one or more parameters of the first activation function and the second activation function, wherein adjusting the one or more parameters comprises adjusting one or more coefficients and mathematical operators, wherein the outcome is associated with healthcare.

An embodiment of a system for performing differential equations network (DEN) computations for a DEN having a plurality of DEN layers, the system comprising a computer system comprising one or more controllers with non-transitory memory stored thereon that when executed enable the controller to obtain, from n input neurons along n dimensions of the DEN, n activation functions for n neurons of a single hidden neural network layer of the DEN, teach each neuron of n neurons one of n activation functions, where each neuron of n neurons of the single hidden neural network layer learns a different activation function of the n activation functions, and predict an outcome based on a combination of outputs from the n neurons. A first example of the system further includes where the n activation functions are based on solutions to a second order linear differential equation. A second example of the system, optionally including the first example, further includes where the n activation functions are based on approximations of one or more of a Gauss Hypergeometric function and a polylogarithm function. A third example of the system, optionally including the first and/or second examples, further includes where the plurality of DEN layers further comprises an input layer comprising the n input neurons and an output layer, and where there are no additional layers other than the input layer, the output layer, and the single hidden neural layer, and where the single hidden neural layer comprises more than one neuron and learns more than one activation function.

An embodiment of a computer-readable storage medium storing computer executable instructions on non-transitory memory thereof, which, when executed by a computer, will cause the computer to perform a method of performing differential equations network (DEN) computations for a DEN having a plurality of DEN layers, the method comprising receiving a plurality of activation functions provided by one or more input neurons of an input DEN layer to a single hidden neural network layer, learning a first activation function via a first neuron of the hidden neural network layer and a second activation function via a second neuron of the hidden neural network layer, and predicting an outcome via a combination of the first and second neurons, the outcome corresponding to a combined output of the first and second neurons relayed to an output DEN layer, and where each of the input DEN layer, the single hidden neural network layer, and the output DEN layer constitute a compact DEN. A first example of the computer-readable storage medium further includes where the first activation function is different than the second activation function. A second example of the computer-readable storage medium, optionally including the first example, further includes where the selecting further includes selecting the first activation function and the second activation function based on an error between the combined output of the first and second neurons and an expected output, where the expected output is based on a desired output of the first and second neurons. A third example of the computer-readable storage medium, optionally including the first and/or second examples, further includes adjusting one or more coefficients and mathematical operators of the first activation function and the second activation functions to decrease the error of the combined output. A fourth example of the computer-readable storage medium, optionally including one or more of the first through third examples, further includes where the first and second activation functions are one or more of ReLU and sigmoid functions. A fifth example of the computer-readable storage medium, optionally including one or more of the first through fourth examples, further includes where the hidden neural network is a single layer, and where the hidden neural network is the only layer with neurons configured to learn activation functions. A sixth example of the computer-readable storage medium, optionally including one or more of the first through fifth examples, further includes where the plurality of activation functions from the one or more input neurons is related to one or more healthcare parameters including age, weight, medications, geographic location, diet, current health status, and daily habits. A seventh example of the computer-readable storage medium, optionally including one or more of the first through sixth examples, further includes where the first and second neurons of the hidden neural layer predict healthcare outcomes for one or more of diabetes, acute respiratory disorder, autoimmune diseases, autocrine diseases, neural diseases, mental health disorder, and cancers. An eighth example of the computer-readable storage medium, optionally including one or more of the first through seventh examples, further includes where the plurality of activation functions from the one or more input neurons are adjusted as the healthcare parameters change.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for performing differential equations network (DEN) computations for a DEN having a plurality of DEN layers comprising only one input layer, only one hidden neural network layer, and only one output layer, where there are no other layers in the DEN other than the input layer, the only one hidden neural network layer, and the output layer, the method comprising:

obtaining, from a plurality of input neurons along a plurality of dimensions of the DEN, a plurality of activation functions for a plurality of neurons of the only one hidden neural network layer of the DEN, wherein each of the plurality of activation functions is different;

selecting a single activation function of the plurality of activation functions to teach a neuron of the plurality of neurons, where each neuron of the plurality of neurons learns a different one of the plurality of activation functions independently of other neurons to provide a compact DEN;

presenting a first activation function to a first neuron of the only one hidden neural network layer, wherein the first activation function is a single activation function, and a second activation function to a second neuron of the only one hidden neural network layer;

learning the first activation function via the first neuron of the only one hidden neural network layer and the second activation function via the second neuron of the only one hidden neural network layer independent of the first neuron, wherein the second activation function is different than the first activation function; and predicting a healthcare outcome via performing DEN computations via a combination of the first and second neurons, the outcome corresponding to a combined output of the first and second neurons relayed to an output DEN layer, wherein each of the input DEN layer, the only one hidden neural network layer, and the output DEN layer constitute a compact DEN.

2. The method of claim 1, wherein the only one hidden neural network layer is a single neural layer comprising each of the plurality of neurons.

3. The method of claim 1, wherein the selecting is based on at least an error between an actual value and the outcome, where the outcome is based on activation functions learned by each of the plurality of neurons.

4. The method of claim 3, wherein the plurality of neurons of the only one hidden neural network layer learn activation functions to decrease the error.

5. The method of claim 1, further comprising decreasing an error of the outcome determined by the first and second neurons via adjusting one or more parameters of the first activation function and the second activation function, wherein adjusting the one or more parameters comprises adjusting one or more coefficients and mathematical operators, and wherein the outcome is associated with healthcare.

6. A system for performing differential equations network (DEN) computations for a DEN having a plurality of DEN layers comprising only one input layer, only one hidden neural network layer, and only one output layer, the system comprising:

a non-transitory computer system comprising one or more controllers with non-transitory memory stored thereon that when executed enable the controller to:

obtain, from a plurality of input neurons along a plurality of dimensions of the DEN, a plurality of activation functions for a plurality of neurons of the only one hidden neural network layer of the DEN, wherein each activation function of the plurality of activation functions is different;

select a first, single activation function of the plurality of activation functions to present to and teach a first neuron of the plurality of neurons;

select a second, single activation function of the plurality of activation functions, different than the first activation function, to present to and teach a second neuron of the plurality of neurons, where each neuron of the plurality of neurons of the only one hidden neural network layer learns a different activation function of the plurality of activation functions independent of the other neurons;

learning the first activation function via the first neuron of the only one hidden neural network layer and the second activation function via the second neuron of the only one hidden neural network layer independent of the first neuron, wherein the second activation function is different than the first activation function; and predicting an outcome via a combination of the first and second neurons, the outcome corresponding to a combined output of the first and second neurons relayed to an output DEN layer, wherein each of the input DEN layer, the only one hidden neural network layer, and the output DEN layer constitute a compact DEN.

7. The system of claim 6, wherein the plurality of activation functions are based on solutions to a second order linear differential equation.

8. The system of claim 6, wherein the plurality of activation functions are based on approximations of one or more of a Gauss Hypergeometric function and a polylogarithm function.

9. The system of claim 6, wherein the only one input layer comprises the plurality of input neurons, wherein there are no additional layers in the plurality of DEN layers other than the input layer, the output layer, and the only one hidden neural layer, and wherein the only one hidden neural layer comprises more than one neuron and learns more than one activation function.

10. A non-transitory computer-readable storage medium storing computer executable instructions on non-transitory memory of the computer-readable storage medium, which, when executed by a computer, will cause the computer to perform a method for predicting a healthcare outcome via performing differential equations network (DEN) computations for a DEN having a plurality of DEN layers comprising only one input layer, only one hidden neural network layer, and only one output layer, the method comprising:

obtaining a plurality of activation functions from one or more input neurons of an input DEN layer;

receiving the plurality of activation functions provided by one or more input neurons of the input DEN layer to the only one hidden neural network layer, wherein each activation function of the plurality of activation functions is different, including selecting a single activation function of the plurality of activation functions to teach each neuron of the single hidden neural network layer;

presenting a first activation function to a first neuron of the only one hidden neural network layer, wherein the first activation function is a single activation function, and a second activation function to a second neuron of the only one hidden neural network layer;

learning the first activation function via the first neuron of the only one hidden neural network layer and the second activation function via the second neuron of the only one hidden neural network layer independent of the first neuron, wherein the second activation function is different than the first activation function; and predicting an outcome via a combination of the first and second neurons, the outcome corresponding to a combined output of the first and second neurons relayed to an output DEN layer, wherein each of the input DEN layer, the single hidden neural network layer, and the output DEN layer constitute a compact DEN.

11. The non-transitory computer-readable storage medium of claim 10, wherein the selecting further includes selecting the first activation function and the second activation function based on an error between the combined output of the first and second neurons and an expected output, and wherein the expected output is based on a desired output of the first and second neurons.

12. The non-transitory computer-readable storage medium of claim 11, further comprising adjusting one or more coefficients and mathematical operators of the first activation function and the second activation function to decrease the error of the combined output.

13. The non-transitory computer-readable storage medium of claim 10, wherein the first and second activation functions are one or more of ReLU and sigmoid functions.

14. The non-transitory computer-readable storage medium of claim 10, wherein the only one hidden neural network is a single layer, and wherein the only one hidden neural network is the only layer with neurons configured to learn activation functions.

15. The non-transitory computer-readable storage medium of claim 10, wherein the plurality of activation functions from the one or more input neurons are related to one or more healthcare parameters including age, weight, medications, geographic location, diet, current health status, and daily habits.

16. The non-transitory computer-readable storage medium of claim 15, wherein the first and second neurons of the hidden neural layer predict healthcare outcomes for one or more of diabetes, acute respiratory disorder, autoimmune diseases, autocrine diseases, neural diseases, mental health disorder, and cancers.

17. The non-transitory computer-readable storage medium of claim 15, wherein the plurality of activation functions from the one or more input neurons are adjusted as the one or more healthcare parameters change.

* * * * *